(12) United States Patent
Palmeri et al.

(10) Patent No.: US 8,118,744 B2
(45) Date of Patent: Feb. 21, 2012

(54) METHODS, SYSTEMS AND COMPUTER PROGRAM PRODUCTS FOR ULTRASOUND SHEAR WAVE VELOCITY ESTIMATION AND SHEAR MODULUS RECONSTRUCTION

(75) Inventors: Mark L. Palmeri, Durham, NC (US); Kathryn R. Nightingale, Durham, NC (US); Gregg E. Trahey, Durham, NC (US); Kristin D. Frinkley, Durham, NC (US)

(73) Assignee: Duke University, Durham, NC (US)

( * ) Notice: Subject to any disclaimer, the term of this patent is extended or adjusted under 35 U.S.C. 154(b) by 839 days.

(21) Appl. No.: 12/028,203

(22) Filed: Feb. 8, 2008

(65) Prior Publication Data
US 2008/0249408 A1    Oct. 9, 2008

Related U.S. Application Data

(60) Provisional application No. 60/900,655, filed on Feb. 9, 2007.

(51) Int. Cl.
*A61B 8/00* (2006.01)
(52) U.S. Cl. ......... 600/437; 600/443
(58) Field of Classification Search .......... None
See application file for complete search history.

(56) References Cited

U.S. PATENT DOCUMENTS

| | | | | |
|---|---|---|---|---|
| 6,270,459 | B1 * | 8/2001 | Konofagou et al. | 600/449 |
| 6,508,768 | B1 * | 1/2003 | Hall et al. | 600/443 |
| 2004/0068184 | A1 * | 4/2004 | Trahey et al. | 600/437 |
| 2004/0167403 | A1 * | 8/2004 | Nightingale et al. | 600/437 |

OTHER PUBLICATIONS

Mark L. Palmeri; "A Finite-Element Method Model of Soft Tissue Response to Impulsive Acoustic Radiation Force"; IEEE Transactions of Ultrasonics, Ferroelectrics, and Frequency Control, vol. 52, No. 10, (Oct. 2005) pp. 1699-1712.
Mark L. Palmeri; "Dynamic Mechanical Response of Elastic Spherical Inclusions to Impulsive Acoustic Radiation Force Excitation"; IEEE Transactions of Ultrasonics, Ferroelectrics, and Frequency Control, vol. 53, No. 11, (Nov. 2006) pp. 2065-2079.
Kathryn Nightingale; "Analysis of Contrast in Images Generated with Transient Acoustic Radiation Force"; Ultrasound in Med. & Biol., vol. 32, No. 1, pp. 61-72, (2006).
Kathryn Nightingale; "Shear-Wave Generation Using Acoustic Radiation Force: in Vivo and Ex Vivo Results"; Ultrasound in Med. & Biol., vol. 29, No. 12, pp. 1715-1723, (2003).
Jeremy J. Dahl; "A Parallel Tracking Method for Acoustic Radiation Force Impulse Imaging"; IEEE Transactions of Ultrasonics, Ferroelectrics, and Frequency Control, vol. 54, No. 2, (Feb. 2007) pp. 301-312.
M.L. Palmeri; "Quantifying Hepatic Shear Modulus in Vivo Using Acoustic Radiation Force" Ultrasound in Med. & Biol., vol. 34, No. 4, pp. 546-558, (2008).

* cited by examiner

*Primary Examiner* — Long V. Le
*Assistant Examiner* — Nicholas Evoy
(74) *Attorney, Agent, or Firm* — Myers Bigel Sibley & Sajovec

(57) ABSTRACT

Methods for determining a mechanical parameter of a sample include detecting shear waves that have been generated in the sample by an applied shear wave source. A time of peak displacement of the shear waves for a plurality of sample positions is determined. At least one mechanical parameter of the sample based on the time of peak displacement for the plurality of sample positions is determined.

22 Claims, 12 Drawing Sheets

(a) $\mu = 1.33$ kPa (b) $\mu = 8$ kPa (c) SHEAR MODULUS VS. BMI

METHODS, SYSTEMS AND COMPUTER PROGRAM PRODUCTS FOR ULTRASOUND SHEAR WAVE VELOCITY ESTIMATION AND SHEAR MODULUS RECONSTRUCTION

RELATED APPLICATIONS

This application claims priority to U.S. Provisional Application Ser. No. 60/900,655 filed Feb. 9, 2007, the disclosure of which is hereby incorporated by reference in its entirety.

STATEMENT OF GOVERNMENT SUPPORT

This invention was made with Government support under grant numbers R01-CA114075 and R01-EB002132 from the National Institute of Health and grant number 2003014921 from National Science Foundation. The Government has certain rights to this invention.

FIELD OF THE INVENTION

The present invention relates to ultrasound techniques for quantifying and/or imaging the stiffness of tissues, organs, and other samples.

BACKGROUND OF THE INVENTION

The quantification of the stiffness of tissues and organs is useful in the clinical setting to track the progression of disease and to monitor the response of diseased tissues to treatments (e.g., drug regimens, diet/lifestyle changes, chemotherapy, and radiotherapy). For example, the liver experiences the deposition of fibrous tissue in response to infections, alcohol, and malignancy. The degree of fibrosis is currently characterized using needle core biopsies and monitoring indirect clinical markers of liver function (e.g., liver transaminases and coagulation factors). Biopsy, however, is severely limited in that it samples an extremely small value of the liver, while fibrosis occurs over the entire organ. Biopsies are also inherently risky, with the chance of bleeding and puncture of critical adjacent organs. Biopsies, therefore, are not performed very frequently, even though the clinician would like to have the ability to more frequently (and accurately) monitor fibrosis in the liver. Better monitoring may assist clinicians in making decisions to initiate certain therapeutic protocols, to perform organ transplants at a given time, and/or to monitor response to treatments. In addition to assessing liver fibrosis, tissue stiffness measurements could also have clinical utility in various diseases and conditions, including but not limited to steatotic (fatty) liver disease, myopathies associated with decreased muscle tone, and to monitor tumor response to chemotherapeutic and/or radiation treatment. ARFI imaging, as described in U.S. Pat. Nos. 6,371,912 and 6,951,544, generate images of relative tissue stiffness by displaying displacement magnitudes in adjacent structures and tissues.

U.S. Pat. No. 7,252,004 discusses using a focused ultrasound compression wave to cause a shear wave in a medium. Unfocused ultrasound compression waves are then emitted at a fast rate to obtain a succession of images in the medium. The images are processed in deferred time in order to determine the movements of the medium during the propagation of the shear wave. However, these processing techniques can be complicated and time intensive.

U.S. Pat. No. 5,606,971 discusses the potential for using shear waves to characterize the stiffness of materials, but it is unclear as to how to perform actual reconstructions from the shear wave data. The shear wave tracking modalities (such as SSI) typically rely on the inversion of the Helmholtz (transverse wave) equation to estimate shear wave velocity. See J. Bercoff, M. Tanter, and M. Fink. "Supersonic shear imaging: A new technique for soft tissue elasticity mapping." IEEE Trans. Ultrason., Ferroelec., Freq. Contr., 51(4): 396-409, 2004. and R. Lerner, S. Huang, and K. Parker. "Sonoelasticity images derived from ultrasound signals in mechanically vibrated tissues." Ultrasound Med. Biol., 16: 231-239, 1990. However, Helmholtz analysis based techniques typically require taking second order displacement derivatives in both space and time. These mathematical operations may amplify noise in the data and make accurate shear wave estimates difficult. Jitter associated with ultrasonically tracking these displacement fields typically requires that significant filtering operations be performed on the displacement data. These filtering operations are computationally intensive and may be difficult to use in real-time processing.

SUMMARY OF EMBODIMENTS ACCORDING TO THE INVENTION

According to embodiments of the present invention, methods for determining a mechanical parameter of a sample include detecting shear waves that have been generated in the sample by an applied shear wave source. A time of peak displacement of the shear waves for a plurality of sample positions is determined. At least one mechanical parameter of the sample based on the time of peak displacement for the plurality of sample positions is determined.

According to certain embodiments of the present invention, the at least one mechanical parameter includes at least one of shear elasticity modulus, Young's modulus, dynamic shear viscosity, shear wave velocity and mechanical impedance of the sample. For example, determining at least one mechanical parameter can include determining a slope of a plurality of times to peak displacement as a function of distance from an origin of the shear wave.

According to certain embodiments of the present invention, the plurality of sample positions includes a plurality of lateral positions at a plurality of distances laterally displaced from an origin of the shear wave. The plurality of lateral positions can include a plurality of datasets, each dataset being obtained at a distance displaced from the origin of the shear wave at a predetermined transverse direction.

According to certain embodiments of the present invention, a regression coefficient threshold to the plurality of times to peak displacement is applied. Determining a slope can include determining a plurality of localized slopes of the times to peak displacements as a function of distance from the origin of the shear wave. In some embodiments, an image based on the plurality of localized slopes can be generated and the localized slopes can represent a spatial change in the mechanical property in the sample.

According to some embodiments of the present invention, the sample is an in vivo human tissue sample. In particular embodiments, the sample is a liver tissue sample.

According to some embodiments of the present invention, the shear waves are detected with an internally inserted ultrasound probe array.

According to some embodiments of the present invention, the shear waves are detected with an externally applied ultrasound array.

According to some embodiments of the present invention, the applied shear wave source is an ultrasound transducer. In certain embodiments, the shear waves are detected by the ultrasound transducer.

According to some embodiments of the present invention, the shear waves are generated by transmitting ultrasound energy into the sample in a first direction to provide a shear wave source that generates an extended shear wave that propagates in a second direction substantially orthogonal to the first direction to cause movement in the first direction of tissue that is offset from the shear wave source in the second direction.

According to certain embodiments of the present invention, the at least one mechanical parameter of the sample is correlated to a measurement of a healthy/diseased tissue state.

According to certain embodiments of the present invention, the at least one mechanical parameter of the sample is monitored as a function of time, and a healthy/diseased tissue state is assessed based on a chance in the at least one mechanical parameter of the sample as a function of time.

According to some embodiments, the plurality of positions is along a central axis of a position of the applied shear wave source.

According to certain embodiments, determining the at least one mechanical parameter of the sample is based on a reference database of experimentally determined or simulated times of peak displacement and associated mechanical properties.

According to some embodiments of the present invention, systems for determining a mechanical parameter of a sample include means for detecting shear waves that have been generated in the sample by an applied shear wave source, means for determining a time of peak displacement of the shear waves for a plurality of sample positions, and means for determining at least one mechanical parameter of the sample based on the time of peak displacement for the plurality of sample positions.

According to some embodiments of the present invention, systems for determining a mechanical parameter of a sample include a shear wave peak displacement module configured to detect shear waves that have been generated in a sample by an applied shear wave source, to determine a time of peak displacement of the shear waves for a plurality of sample positions, and to determine at least one mechanical parameter of the sample based on the time of peak displacement for the plurality of sample positions.

According to some embodiments of the present invention, a computer program product for determining a mechanical parameter of a sample includes computer readable storage medium having computer readable program code embodied therein. The computer readable program code includes computer readable program code for detecting shear waves that have been generated in the sample by an applied shear wave source, computer readable program code for determining a time of peak displacement of the shear waves for a plurality of sample positions, and computer readable program code for determining at least one mechanical parameter of the sample based on the time of peak displacement for the plurality of sample positions.

BRIEF DESCRIPTION OF THE DRAWINGS

FIG. 8($b$) is a graph of the reconstructed shear moduli over depths from 16-20 mm (focal depth) using the lateral TTP calculation on the simulated datasets for 1.33 (x) and 2.83 (o) kPa shear moduli. The non-tracked FEM data are represented by the solid lines as indicated in the legend of FIG. 8($a$), with the mean±one standard deviation shear modulus estimates over the range of depths represented in the text box. The corresponding tracked data, using 20 independent speckle realizations, is shown in the corresponding dashed lines as indicated in the legend of FIG. 8($a$) (mean±one standard deviation), for the 1.33(x) and 2.82 (o) kPa media.

In FIG. 10($a$), the TTP displacement is estimated over the region of interest (ROI). FIG. 10($b$) graphs locally estimated shear wave speeds by taking the inverse of the slope of the TTP at each pixel as a function of lateral position for each depth, with a sliding window for linear regression. In FIG. 10($c$), a localized shear modulus image is obtained using the lateral-TTP calculation.

FIG. 11($b$) is a graph of the motion-filtered displacement as a function of time at the focal depth, representing one of the many depth increments analyzed over the DOF of the excitation beam.

FIGS. 11(c) and 11(d) are graphs of the time to peak displacements (ms) as a function of lateral position (mm) before a goodness of fit calculation (FIG. 11(c)) and after application of a goodness of fit metrics ($R^2 > 0.8$, 95% CI<0.2) (FIG. 11(d)).

FIG. 11(e) is a box plot graph of the reconstructed shear moduli from the six independent data acquisitions in the human volunteer. The box plots represent the distribution of shear moduli over the DOF, with each box representing the interquartile range (IQR) of reconstructed moduli with the horizontal line representing the median value. The whiskers represent ±1.5 IQR, with outliers indicated by a "+" symbol.

In FIGS. 12(a) and 12(b), the reconstructed shear moduli represent the mean and standard deviation over six independent measurements. Values that did not meet the goodness of fit parameters ($R^2 > 0.8$, 95% CI<0.2) or were greater than one standard deviation from the mean for a given measurement were excluded from the analysis.

DETAILED DESCRIPTION OF EMBODIMENTS ACCORDING TO THE INVENTION

Figure 2:
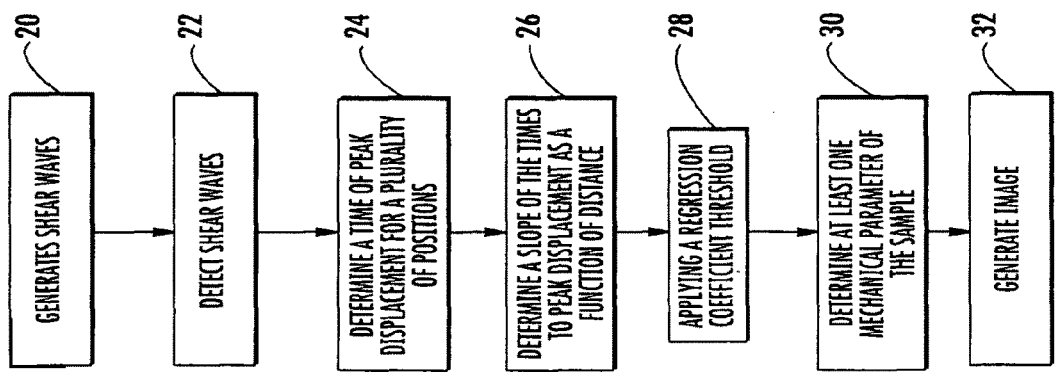
FIGS. 1 and 2 are flowcharts illustrating operations according to embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a "first" element, component, region, layer or section discussed below could also be termed a "second" element, component, region, layer or section without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

Figure 1:
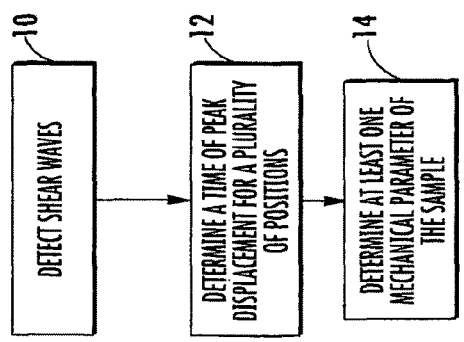

According to embodiments of the current invention, as shown in FIG. 1, a mechanical parameter of a sample can be determined by detecting the shear waves (block 10) that have been generated in the sample by an applied shear wave source. In particular, a time of peak displacement of the shear waves for a plurality of sample positions can be determined (block 12) to provide a plurality of peak displacement times as a function of position. At least one mechanical parameter of the sample is determined based on the time of peak displacement from the plurality of sample positions (block 14). The mechanical parameters can include the shear elasticity modulus, Young's modulus, dynamic shear viscosity, the shear wave velocity, the mechanical impedance of the sample, density, Poisson's ratio and other mechanical parameters.

In particular embodiments shown in FIG. 2, shear waves are generated in a sample (block 20). For example, shear waves can be generated by transmitting ultrasound energy into the sample in a first direction to provide a shear wave source that generates an extended shear wave that propagates in a second direction substantially orthogonal to the first direction to cause movement in the first direction of tissue that is offset from the shear wave source in the second direction. A time of peak displacement of the shear waves for a plurality of sample positions can be determined (block 22), for example, using ultrasound tracking techniques. A time of peak displacement of the shear waves for a plurality of positions can be determined (block 24). A slope of the times to peak displacement can be determined as a function of the distance from an origin of the shear wave (block 26). In some embodiments, a regression coefficient threshold can be applied to determine the slope of the times to peak displacement as a function of distance from the origin of the shear wave (block 28).

At least one mechanical parameter of the sample can be determined based on the time of peak displacement for the plurality of sample positions (block 30). For example, mechanical parameters of the sample may be related to the slope of the times to peak displacement is a function of distance from the origin of the shear wave. In some embodiments, and image may be generated (block 32). For example, a plurality of localized slopes of the times to peak displacements as a function of distance from the origin of the shear waves can be determined, and an image can be formed based on the plurality of localized slopes. A change in the slope can represent a spatial change in the mechanical property of the sample.

Figure 3:
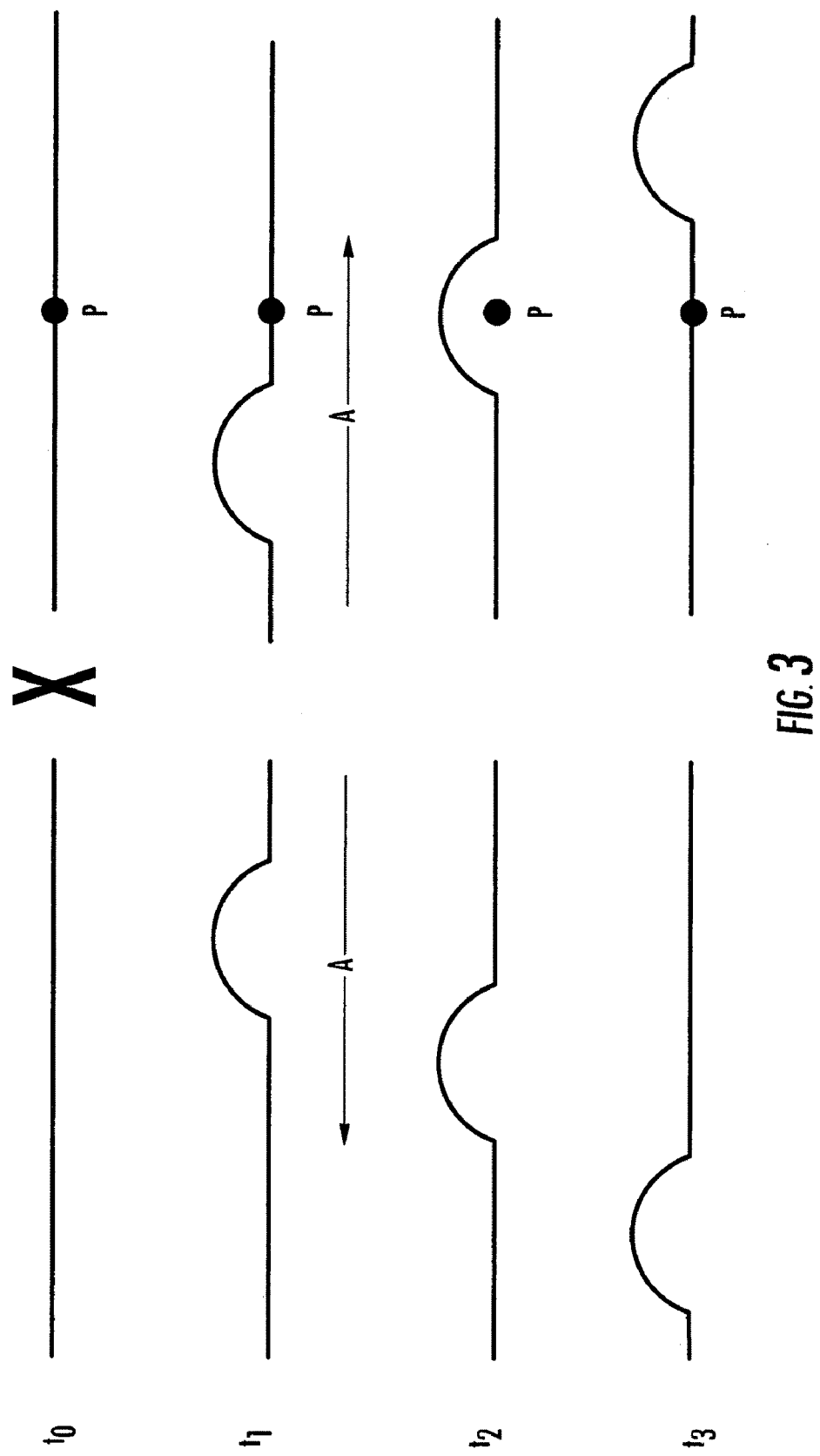
FIG. 3 is a schematic diagram illustrating the propagation of a shear wave in tissue as a function of time in response to a shear wave excitation force according to embodiments of the current invention.

FIG. 3 is a schematic illustration of the propagation of a shear wave in tissue at times $t_0$, $t_1$, $t_2$, and $t_3$. At time $t_0$, a shear wave excitation source is applied to the tissue at position X. As a resulting shear wave travels along opposing axial direction A (a direction orthogonal to the shear wave source) towards position P at time $t_1$. The peak displacement of the shear wave at position P occurs at time $t_2$. At time $t_3$, the shear wave has traveled past position P. Therefore, the time of peak displacement illustrated in FIG. 3 is at time $t_2$. Accordingly, the time to peak displacement for a plurality of positions P can be used to determine a mechanical parameter in a sample, such as biological tissue, and may be less computationally intensive than previous techniques and/or have a higher signal-to-noise ratio (SNR).

Figure 4:
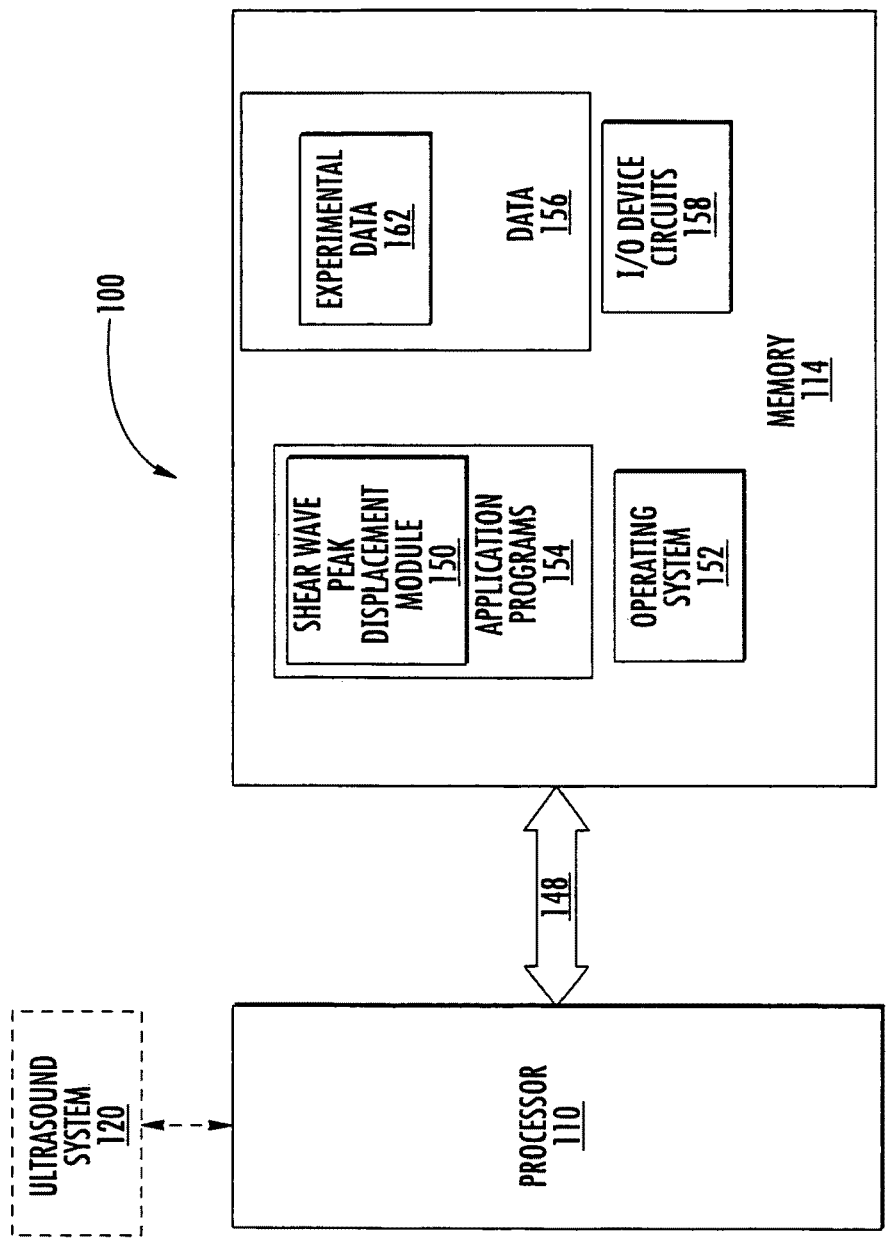
FIG. 4 is a schematic diagram of systems and computer program products according to embodiments of the current invention.
Figure 5:
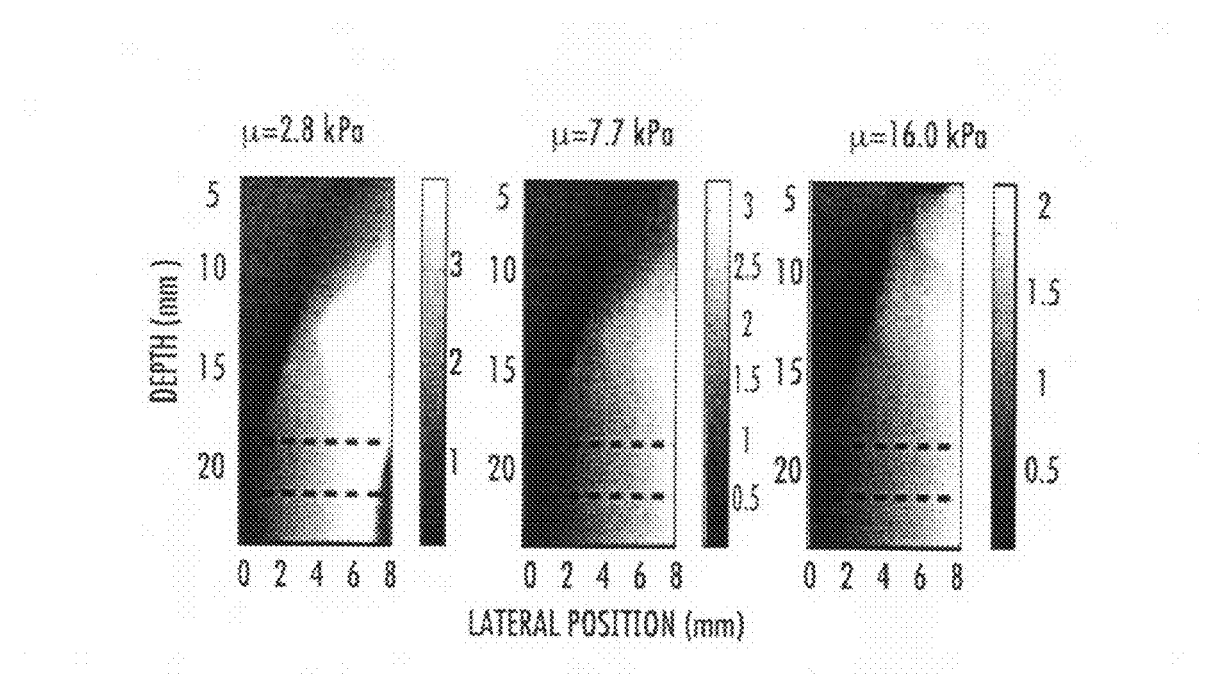
FIG. 5 is a graph of the time to peak displacement along the imaging plane in finite element method (FEM) data from simulated elastic materials with a shear moduli of 2.8, 7.7, and 16.0 kPa. The horizontal dashed lines represent the depth of field (DOF) over which shear wave reconstructions were performed on data in FIGS. 6-12. The shaded bar represents time to peak displacement (TTP) in milliseconds, and a lateral position of zero corresponds to the center of the region of excitation (ROE).

Although FIG. 3 is illustrated with a position P that is laterally displaced from the excitation source position X (i.e., perpendicular to the direction of the applied excitation source), it should be understood that the position P may also be along a central axis of the position X of the applied shear wave source. In other words, the position P can be in-line or parallel to the direction of the excitation source. FIG. 4 is a block diagram of exemplary embodiments of data processing systems that illustrates systems, methods, and computer program products in accordance with embodiments of the present invention. As shown in FIG. 4, a data processing system 100 includes a processor 110, and is in communication with ultrasound system 120. The ultrasound system 120 can include transducer arrays configured to apply a shear wave force and/or detect shear waves in a sample, such as a biological tissue sample.

The processor 110 communicates with the memory 114 via an address/data bus 148. The processor 110 can be any commercially available or custom microprocessor. The memory 114 is representative of the overall hierarchy of memory devices containing the software and data used to implement the functionality of the data processing system 100. The memory 114 can include, but is not limited to, the following types of devices: cache, ROM, PROM, EPROM, EEPROM, flash memory, SRAM, and DRAM.

As shown in FIG. 4, the memory 114 may include several categories of software and data used in the data processing system 100: the operating system 152; the application programs 154; the input/output (I/O) device drivers 158; a shear wave peak displacement module 150 and the data 156. The data 156 may include experimental data 150 (which can include electrical signals from the ultrasound system 120).

As will be appreciated by those of skill in the art, the operating system 152 may be any operating system suitable for use with a data processing system, such as OS/2, AIX, OS/390 or System390 from International Business Machines Corporation, Armonk, N.Y., Windows CE, Windows NT, Windows95, Windows98 or Windows2000 from Microsoft Corporation, Redmond, Wash., Unix or Linux or FreeBSD, Palm OS from Palm, Inc., Mac OS from Apple Computer, or proprietary operating systems. The I/O device drivers 158 typically include software routines accessed through the operating system 152 by the application programs 154 to communicate with devices such as I/O data port(s), data storage 156 and certain memory 114 components and/or the ultrasound system 120. The application programs 154 are illustrative of the programs that implement the various features of the data processing system 100 and can include at least one application which supports operations according to embodiments of the present invention. Finally, the data 156 represents the static and dynamic data used by the application programs 154, the operating system 152, the I/O device drivers 158, and other software programs that may reside in the memory 114.

The shear wave peak displacement module 150 can be configured to perform operations according to embodiments of the present invention. For example, the shear wave peak displacement module 150 can be configured to control the ultrasound system 120 and/or to obtain data from the ultrasound system 120. In particular embodiments, the shear wave peak displacement module 150 is configured to generate shear waves, e.g., in a tissue sample by transmitting ultrasound energy into the sample in a first direction to provide a shear wave source that generates an extended shear wave that propagates in a second direction substantially orthogonal to the first direction to cause movement in the first direction of tissue that is offset from the shear wave source in the second direction.

The shear wave peak displacement module 150 can be configured to process ultrasound data, such as shear wave tracking data, to determine a time of peak displacement using the techniques described herein. The shear wave peak displacement module 150 can determine a time of peak displacement of the shear waves for a plurality of sample positions, for example, using ultrasound tracking techniques.

While the present invention is illustrated, for example, with reference to the shear wave peak displacement module 150 being an application program in FIG. 4, as will be appreciated by those of skill in the art, other configurations may also be utilized while still benefiting from the teachings of the present invention. For example, the shear wave peak module 150 may also be incorporated into the operating system 152, the I/O device drivers 158 or other such logical division of the data processing system 100. Thus, the present invention should not be construed as limited to the configuration of FIG. 4, which is intended to encompass any configuration capable of carrying out the operations described herein.

The I/O data port can be used to transfer information between the data processing system 100 and the ultrasound system 120 or another computer system or a network (e.g., the Internet) or to other devices controlled by the processor. These components may be conventional components such as those used in many conventional data processing systems that may be configured in accordance with the present invention to operate as described herein. Therefore, the shear wave peak displacement module 150 can be used to analyze experimental data 162 that has been previously collect and/or experimental data 162 that is collected from the ultrasound system 120.

As an example, the stiffness in the tissue sample can be evaluated through measurement of shear wave velocity because the shear modulus of a material is related to the square of the shear wave velocity. Shear waves may be generated when an impulse excitation acoustic radiation force is applied to a material, such as is done with ARFI imaging (see U.S. Pat. Nos. 6,371,912; 6,951,544 and 6,764,448). Shear waves can be monitored in the tissue through time after the excitation force has been applied, and the shear wave velocity and associated shear modulus of the tissue can be reconstructed from this data.

According to embodiments of the invention, shear waves that have been generated in the sample by an applied shear wave source, such as acoustic radiation force, are detected, for example, by an ultrasound transducer provided as part of the ultrasound system 120. The time of peak displacement of the shear waves for a plurality of sample positions can be determined, and a mechanical parameter of the sample can be determined based on the time of peak displacement for the plurality of sample positions. The resulting data may have less noise that is typically present using previous techniques (such as using an inversion of the Helmholtz equation to estimate shear wave velocity). Moreover, the mechanical parameters, such as the shear wave velocity, may be independent of the magnitude of the shear wave source.

For example, the time to peak displacement for a plurality of sample positions can be plotted by the shear wave peak displacement module 150 as a function of distance from the origin of the shear wave. The time to peak displacement generally increases for positions that are further away from the origin of the shear waves. The slope of the times to peak displacement as a function of distance from the origin of the shear wave can be used as a measurement of a mechanical parameter, such as shear wave velocity.

In particular embodiments, the times to peak displacement are estimated by the shear wave peak displacement module 150 as a function of lateral position. A linear regression can be performed on this data, with a first-order coefficient of the regression line (lateral position/time to peak displacement) representing the shear wave speed. For depths other than the focal depth, where the angle of shear wave propagation is generally not parallel in the lateral dimension, a correction factor compensating for the non-parallel alignment may be applied to the estimated shear wave velocity. The zeroth order coefficient represents the time to peak displacement at the focal depth, which provides another measure of the shear wave speed as predicted according to embodiments of the current invention. The time to peak displacement techniques described herein can also be applied to the elevation dimension of the sample when displacement estimation is possible in that dimension, such as with a three-dimensional ultrasound transducer.

In some embodiments, the dataset of the time to peak displacement can be used to quantify the stiffness of tissues and/or organs, which may be useful in the clinical setting to track the progression of disease and to monitor the response of diseased tissues to treatments (e.g., drug regimens, diet/lifestyle changes, chemotherapy, and radiotherapy). The techniques described herein can be used to characterize the stiffness of biological tissues using their dynamic displacement response to impulsive acoustic radiation force excitations. This may allow for absolute and relative quantification of tissue stiffness to aid in clinical treatment of a variety of pathologic conditions, such as liver disease (e.g., liver steatosis, liver fibrosis and cirrhosis), atherosclerosis, benign prostatic hypertrophy (BPH) muscular dystrophy, products of ablation, cancer in various organs/tissue, thyroid disease and/or skin diseases. Accordingly, the tissue sample may be an in vivo human tissue sample, such as liver tissue sample. The shear waves can be detected and/or generated using an internally inserted ultrasound probe array (such as an ultrasound probe array configured for insertion into an orifice of the body) or with an externally applied ultrasound array.

The mechanical parameter(s) of the sample can be correlated to measurement of healthy/diseased tissues states, such as by using actual clinical data and known healthy/diseased tissues states. The clinical data can be based on other factors such as demographic information, e.g., age, gender and race, to correlate the measurement of the mechanical parameter(s) with a measurement of healthy/diseased tissues states in a particular demographic group.

In some embodiments, the mechanical parameter(s) of the sample can be monitored as a function of time by performing the shear wave peak displacement techniques on a sample repeatedly over a period of time. A healthy/diseased tissue state determination can be based on a change in the mechanical parameter(s) as a function of time. For example, the mechanical parameter(s) can be monitored over a period of minutes, hours, days, weeks, months or even years to determine the progression of the disease and/or the efficacy of treatment.

The excitation of the tissue with acoustic radiation force and ultrasonic tracking of the resulting displacements can be performed using a single ultrasonic array with electronic focusing, which may be provided as part of the ultrasound system 120 of FIG. 4. The ultrasound system 120 may apply focused acoustic radiation force excitations impulsively (e.g., less than 1 ms) to the tissue. After the radiation force excitation, the resulting tissue displacements can be ultrasonically estimated as a function of depth and time, for example, for up to 10 ms or more. This displacement tracking may be performed both at the location of excitation, and locations spatially offset from the excitation, either using a parallel receive scheme or multiple excitation/displacement tracking location combinations, or a combination of the two schemes. Displacements can be estimated by the shear wave peak displacement module 150 using correlation-based methods or phase-shift calculations. The displacement data can be temporally upsampled, for example, to about 50 kHz, using spline interpolation. Displacement data processed at a given depth may be averaged over several axial samples spanning fractions of a millimeter to reduce jitter in the displacement estimates and to reduce shearing-related bias in the focal zone. Shear wave velocity ($c_T$) estimates may be made using one or more or a combination of the following techniques:

1. The time to peak displacement at the excitation focus is estimated using the displacement data. The shear wave speed is then estimated by either 1) dividing the excitation beamwidth by this time-to-peak displacement. The excitation beamwidth is approximated by $$\frac{\lambda z}{d},$$

where $\lambda$ is the ultrasonic wavelength, z is the focal depth, and d is the active aperture width, or 2) comparing this time with a look up table or reference database of expected times for different material properties, based upon the specific ultrasonic parameters implemented for excitation and tracking. The reference database can be an experimentally determined database and/or based on simulated data from calculations and can be used to approximate properties of a material.

2. At a given depth, the times to peak displacement are estimated as a function of lateral position. A linear regression is performed on this data, with the first-order coefficient of this regression line (lateral position/time to peak displacement) representing the shear wave speed. For depths other than the focal depth, where the angle of shear wave propagation is not parallel to the lateral dimension, a correction factor compensating for this non-parallel alignment is applied to the estimated shear wave velocity. The zeroth-order coefficient represents the time-to-peak displacement at the focal depth, which provides another measure of the shear wave speed as predicted in the first calculation.

If a constant density ($\rho$) and shear modulus (G) is assumed over the volume of tissue between the region of excitation (ROE) and the more spatially-offset tracked locations, then the shear modulus over this volume of tissue can be estimated using the expression. Shear wave estimations can be made in multiple locations of 2D or 3D maps of shear modulus with each excitation location yielding an estimate over an area of approximately 10-50 mm$^2$, which is dictated by the lateral propagation distance of the induced shear waves and the depth of the excitation. Since the same hardware may be used for B-mode imaging, ARFI imaging, and the techniques described herein, all three types of data maps and images could be generated concurrently to help aid clinical diagnoses, and the estimated moduli can be correlated with displacement amplitudes.

In some embodiments, the slope of the times to peak displacement may change over the region of interest, for example, if the mechanical parameters of the sample change over the region of interest. In some embodiments, the shear wave peak displacement module 120 can use these changes to create an image, for example, by determining a plurality of different, localized slopes as a function of position. These localized changes in the slope as a function of position can indicate a spatial change in the shear wave velocity or other mechanical parameter of the sample.

According to some embodiments of the current invention, acoustic radiation force is used to generate the shear waves in the target organ or tissue. Various shear wave generation techniques may be used, including those described in U.S. Pat. No. 6,764,448. The use of acoustic radiation force generally does not require mechanical coupling between an external vibrator and the target organ or tissue. Radiation force excitations may be possible in all organs or tissue where current ultrasound images are possible. The same ultrasound transducer (e.g., in the ultrasound system 120) may be used to generate the excitation and track the resulting shear wave displacements, which can reduce or eliminate errors due to spatial misalignment.

In addition to using the time to peak (TTP) displacement measurements at locations spatially offset from the shear wave source (the excitation) to estimate the shear wave velocity, embodiments of the invention can address reconstructing a metric within the region of excitation (ROE) down the axis of excitation (generally referred to as "on axis" measurements). TTP metrics can be used down the lateral/elevation axis of symmetry in the ROEs for shear wave sources, along with the TTP values that are adjacent to this axis, but still within the ROE. The spatial extent of the excitation source generally cannot be described analytically and may be estimated in both the lateral and elevation dimensions, as a function of depth relative to the focal depth, by using one or more of the following methods: (1) simulation, (2) the measured width of the shear waves outside the ROE, (3) approximation based on the geometry of the active aperture of the ultrasound array.

Accordingly, "on axis" measurements may result in (1) greater displacement magnitudes within the ROE, leading to greater signal to noise ratios (SNR), (2) reduced computational demands. The greater SNR can reduce the amount of filtering that needs to be performed, leading to more accurate shear wave speed estimates. The reduced computational demands may result from the fact that the spatial extent of the excitation are independent of the stiffness of the material/tissue being imaged, and TTP measurements can be directly related to shear wave speeds without needing to perform linear regressions.

When using TTP measurements within the ROE that are not directly on the axis of symmetry, compensation may be made for the direction of wave propagation. Outside of the depth of field (near the focal point), the direction of wave propagation is typically not purely orthogonal to the axis of symmetry. Such compensatory calculations may be derived from (1) simulations and/or (2) geometric corrections based on the active aperture of the ultrasound array.

Embodiments according to the present invention will now be described with respect to the following non-limiting example.

Example

Time to peak (TTP) displacement data in response to impulsive acoustic radiation force outside the region of excitation (ROE) are used to characterize the shear wave speed of a material, which is used to reconstruct the material's shear modulus. The calculation is developed and validated using finite element method (FEM) simulations. Using this calculation on simulated displacement fields, reconstructions for materials with shear moduli (μ) ranging from 1.3-5 kPa are accurate to within 0.3 kPa, while stiffer shear moduli ranging from 10-16 kPa are accurate to within 1.0 kPa. Ultrasonically tracking the displacement data, which introduces jitter in the displacement estimates, does not impede the use of this calculation to reconstruct accurate shear moduli. Using in vivo data acquired intercostally in 20 volunteers, liver moduli have been reconstructed between 0.9 and 3.0 kPa, with an average precision of ±0.4 kPa. These reconstructed liver moduli are consistent with those reported in the literature(μ=0.75-2.5 kPa) with a similar precision (±0.3 kPa). Repeated intercostal liver shear modulus reconstructions were performed on 10 different days in 2 volunteers over a 105 day period, yielding an average shear modulus of 1.9±0.50 kPa (1.3-2.5 kPa) in the first volunteer, and 1.8±0.4 kPa (1.1-3.0 kPa) in the second volunteer. The simulation and in vivo data to date demonstrate that these techniques are capable of generating accurate and repeatable liver stiffness measurements and appears promising as a clinical tool for quantifying liver stiffness.

Impulsive acoustic radiation force excitations can be generated in tissue at remote, focused locations, and the resulting dynamic tissue response can be monitored using ultrasonic correlation-based methods. The rate at which tissue responds to an impulsive excitation, including the speed at which shear waves propagate away from the region of excitation (ROE), can be measured to quantify the tissue's shear modulus. The use of focused acoustic energy can be used to provide mechanical excitation directly to the focal region of the acoustic beam and generating shear waves directly in the tissue of interest. Impulsive acoustic radiation force excitations generate shear waves within tissues (Sarvazyan et al., 1998). The speed at which these shear waves propagate away from the ROE is related to the shear modulus and density of the tissue; therefore, measuring this shear wave speed facilitates estimation of the tissue's shear modulus.

An imaging system is presented that is capable of generating and monitoring radiation force-induced shear waves in human liver in vivo, along with a robust calculation for reconstructing shear wave speeds from ultrasonically detected displacements to quantify shear moduli. The implementation of the calculation, along with describing the simulation and experimental setups used to quantify the accuracy and precision of the calculation in the clinical context of quantifying liver stiffness, is presented. The calculation is applied to simulation data, experimental phantom data, and in vivo human liver data. The human studies were performed in 20 volunteers, with the repeatability of this shear modulus reconstruction approach studied in two volunteers over a 105 day period. Additional approaches to optimize this calculation, an outline of ongoing studies are explored.

Shear Waves: Generation and Reconstruction In linear, isotropic, elastic solids, the speed of shearwave propagation ($C_T$) is related to shear modulus (μ) and density (ρ) by:

$$C_T = sqrt(\mu/\rho) \quad (1)$$

Equation 1 provides a relationship between shear wave speed and shear modulus; however there are two challenges to using this relationship to characterize the modulus of soft tissue; (1) generating shear waves within tissues in vivo, and (2) reconstructing $c_T$ from measured displacement fields.

Shear Wave Generation Generating shear waves within tissues can be accomplished by coupling external mechanical sources through the skin into the organ of interest or generating the shear wave within tissues using acoustic radiation force. The FibroScan® system (EchoSens, Paris, France) uses an external vibrator to generate shear waves in tissue and has successfully quantified differences in liver stiffness as correlated with fibrosis stage (Sandrin et al., 2003). Similar approaches of external shear wave excitation have also been used in MR-based elastography techniques (Roiviere et al., 7 2006). While these findings are promising, such setups can be challenged in their ability to couple enough energy through the skin and subcutaneous fat to generate adequate shear wave displacements within organs such as the liver, especially in obese patients. External mechanical excitation sources can also be limited by the ribs when trying to reach more superior and lateral regions of the liver.

Some of these challenges can be overcome with the use of focused acoustic radiation force excitations where mechanical excitation occurs along the acoustic wave propagation path and within the focal region of the acoustic beam. These radiation force excitations generate shear waves directly in the tissue of interest. Acoustic radiation force is applied to absorbing and/or reflecting materials in the propagation path of an acoustic wave. This phenomenon is caused by a transfer of momentum from the acoustic wave to the propagation medium. The spatial distribution of the radiation force field (i.e., the region of excitation, or ROE) is determined by both the acoustic excitation parameters and the tissue properties. In soft tissues, where the majority of attenuation results from absorption (Parker, 1983; Christensen, 1988), the following equation can be used to determine radiation force magnitude (Torr, 1984, Nyborg, 1965):

$$F = W_{absorbed}/c = 2\alpha I/c \quad (2)$$

where F [dyn (1000 cm)−3], or [kg s−2 cm−2], is acoustic radiation force (in the form of a body force), $W_{absorbed}$ [W (100 cm)−3] is the power absorbed by the medium at a given spatial location, c [m s−1] is the speed of sound in the medium, α[cm−1] is the absorption coefficient of the medium, and I[Wcm−2] is the temporal average intensity at a given spatial location. The spatial extent of the ROE varies with focal characteristics and tissue attenuation; however, it is always distributed within the geometric shadow of the active transmit aperture and is typically most energetic within the focal region of the acoustic beam.

Shear Wave Reconstruction After shear waves are generated or coupled into the organ of interest, and the tissue displacement response has been measured, there are multiple methods that can be used to estimate the shear wave speed. One method to estimate shear wave speed from dynamic tissue displacement data (~u) involves algebraic inversion of the Helmholtz equation (Oliphant et al., 2001; Bercoff et al., 2004):

$$\rho \partial_2 \sim u_i(\sim x) \partial t_2 = \mu \sim \nabla_2 \sim u_i(\sim x) \quad (3)$$

This method has been successfully applied when ultrasound or magnetic resonance imaging has been used to track tissue displacements (Oliphant et al., 2001; Bercoff et al., 2004; Sandrin et al., 2002; Nightingale et al., 2003), but as Equation 3 indicates, second-order spatial and temporal derivatives of displacement are required for the shear wave speed reconstruction. Given the jitter that exists when ultrasonically estimating displacement, appreciable filtering and smoothing of displacement data must be performed prior to processing (Oliphant et al., 2001; Bercoff et al., 2004). The benefit of this method is that no a priori assumption about shear wave propagation direction needs to be made when analyzing a given region of dynamic displacement data.

Ideally, shear wave speeds would be reconstructed from high signal-to-noise ratio (SNR), three dimensional displacement data using inversion of the Helmholtz equation, allowing for good spatial resolution. However, in our experience, the typically low SNR displacement data obtained with ultrasonic displacement tracking in a single imaging plane yield inaccurate results when relying on second-order differentiation of displacement data. This has motivated the development of alternate methods to reconstruct shear wave speeds in response to impulsive radiation force excitations.

"Time of flight" methods track the position of shear waves through time and correlate their space/time coordinates to estimate shear wave speeds. McLaughlin et al. (2006a) have implemented such an approach using correlation methods on displacement datasets to determine the position of the shear wave, and shear wave speeds are estimated by inverting Eikonal equations that rely on first-order differentiation of shear wave positions through time (McLaughlin and Renzi, 2006a,b).

The Lateral TTP calculation developed herein is a "time of flight" method. In order to make the calculation robust in the presence of noise, the following assumptions are made: (1) homogeneity of the region adjacent to the ROE, (2) shear wave propagation exclusively in the lateral direction (perpendicular to the ROE axis of symmetry), and (3) negligible dispersion over the analyzed region. In this calculation (referencing FIGS. 5-8), shear wave position is estimated by quantifying the TTP displacement at laterally-offset positions outside of the ROE. Calculations are performed over the depth of field (DOF) of the focused radiation force excitation to satisfy the assumption of shear wave propagation in the lateral direction. Using TTP displacements to estimate shear wave speed assumes that the shear wave's peak displacement propagates at the shear wave group velocity through the analyzed region, which is the case for purely elastic or mildly dispersive media. Linear regressions are then performed on the TTP displacement data versus lateral position. The $R^2$ value of the linear regression and the associated 95% confidence interval are used as goodness of fit metrics to exclude datasets corrupted by motion, noise, or other artifacts. The inverse slopes of the remaining lines represent the shear wave speeds and can be used to estimate the shear moduli of the material as a function of depth.

Calculation Implementation The Lateral TTP calculation (FIGS. 5-8) was applied to radiation force-generated, ultrasonically-tracked axial displacement data monitored through time at laterally offset locations in the imaging plane relative to a fixed excitation location. In order to satisfy the assumption of uniform shear wave propagation parallel to the lateral dimension, the axial extent of the data utilized to estimate the shear wave speed was confined to be within the depth of field (DOF) of the excitation beam, as demonstrated in FIG. 5. The DOF was defined by $8(F/\#)2\lambda$, where F/# and $\lambda$ represent the focal configuration and wavelength of the excitation beam, respectively. The dimensionless excitation beam f-number (F/#) was defined as z d, where z was the excitation focal depth, and d was the electronically active aperture width of the excitation beam. At each lateral location, the DOF was subdivided into 0.5 mm in 11 increments for analysis, with the displacement averaged over ±0.25 mm at each depth to reduce jitter/noise. (No axial averaging was performed on FEM model datasets without simulated tracking.) This DOF is indicated by the horizontal dashed lines in the simulated TTP displacement data in FIG. 5. The TTP displacement was estimated from these displacement through time data after upsampling to 50 kHz using low-pass interpolation.

The rate at which TTP displacement changes with lateral position was evaluated using linear regression. Regressions were performed starting one excitation beam width from the center of the ROE and extended over a lateral range where the peak displacements remained above 1 μm. The 1 μm threshold was chosen to ensure a peak displacement estimate SNR of at least 2 dB, as demonstrated in FIG. 6. The inverse slopes of these regression lines, with goodness of fit metrics exceeding a threshold ($R2>0.8$, 95% $CI<0.2$), represent the material's local shear wave speeds (FIG. 4). These specific goodness of fit metrics were applied to all of the datasets presented throughout this manuscript. The interrogated material's density was assumed to be 1.0 g/cm3, and the material's shear modulus was then estimated using Equation 1. Young's moduli (E) could be estimated by $E=2(1+v)\mu=3\mu$, where $v=0.5$ is an incompressible material's Poisson's ratio, but only values for shear modulus ($\mu$) are quoted herein.

Figure 7:
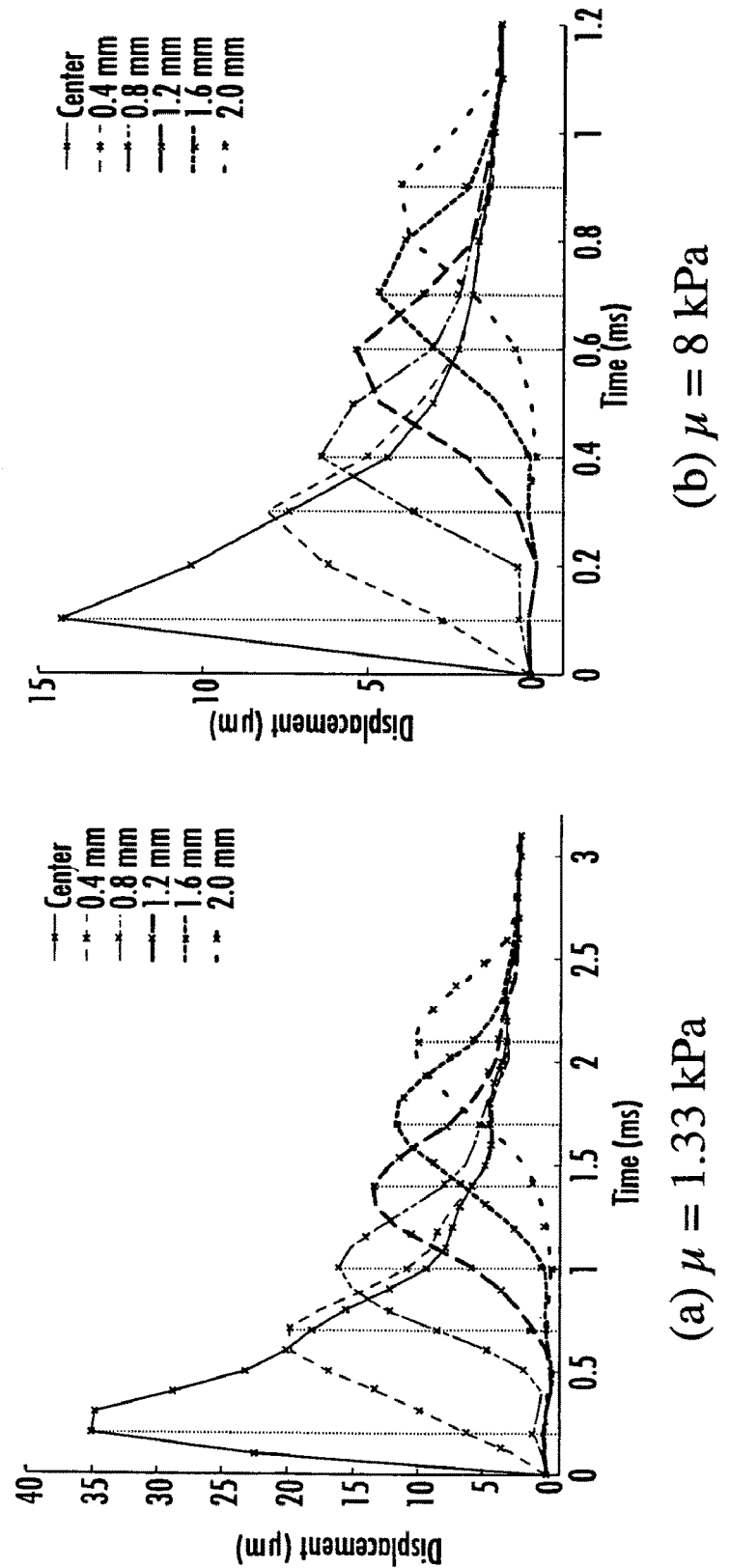
FIGS. 7($a$) and 7($b$) are graphs of simulated displacements ($\mu$m) as a function of time (ms), without ultrasonic tracking, at lateral positions offset from the excitation location for elastic media with shear moduli of 1.33 kPa (FIG. 7($a$)) and 8 kPa (FIG. 7($b$)). The curve appears more finely sampled in the more compliant medium of FIG. 7($a$) due to its slower propagation speed and the fixed 10 kHz temporal sampling (simulating a fixed pulse repetition frequency (PRF) in the experimental system).
Figure 8:
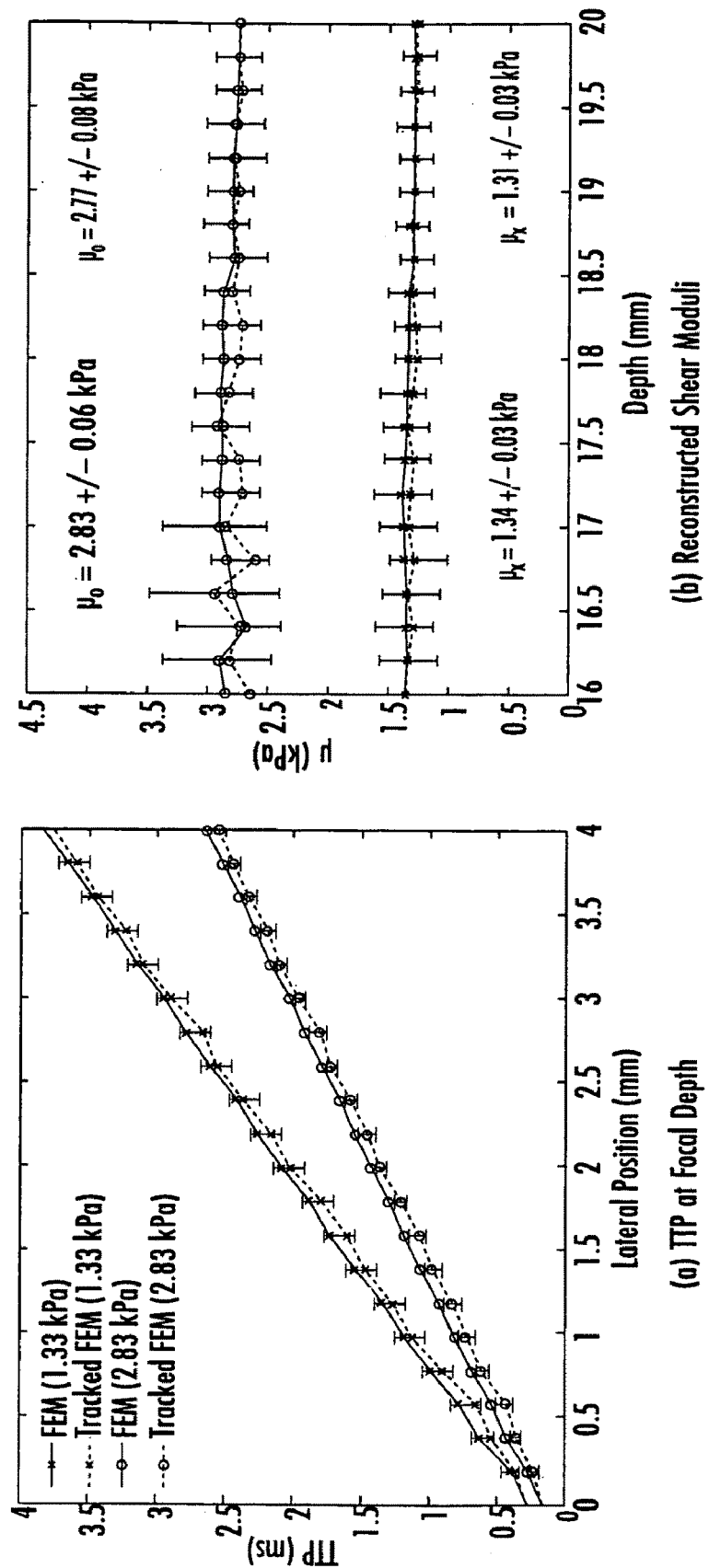
FIG. 8($a$) is a graph of the time to peak (TTP) displacement data at the focal depth (20 mm) as a function of lateral position in simulation data for elastic materials with shear moduli of 1.33 and 2.83 kPa. The inverse slopes of these lines represent the shear wave speeds in these materials.

This procedure is graphically demonstrated in FIG. 7 using the simulation data sampled at 10 kHz. (Note that these data would be upsampled to 50 kHz before being processed with the Lateral TTP calculation.) When two adjacent time steps happened to yield the same peak displacement values, the smaller time step was chosen.

Numerical Methods Three-dimensional Finite Element Method (FEM) models of the dynamic response of elastic media to impulsive acoustic radiation force excitations were used to study the accuracy of the proposed method in reconstructing shear moduli ranging from 1.3-16 kPa. These shear moduli represent those reported for healthy through cirrhotic livers (Foucher et al., 2006; Sandrin et al., 2003). These models have been previously validated to accurately simulate shear waves that are generated in response to impulsive acoustic radiation force excitations in elastic media (Palmeri et al., 2005). Table 1 outlines the simulated excitation beam configuration.

TABLE 1

|  | Excitation | Tracking |
|---|---|---|
| Transmit Focal Depth (mm) | 20 | 20 |
| Receive Focal Depth |  | Dynamic |
| Transmit F/# | 1.3 | 1.0 |
| Receive F/# |  | 0.5 |
| Frequency (MHz) | 6.7 | 6.7 |
| Elevation Focus (mm) | ~19 | ~19 |
| Lateral Line Spacing (mm) |  | 0.2 |
| PRF of Track Lines (kHz) |  | 10 |

The impact of ultrasonically tracking the axial components of simulated displacement fields was also characterized using previously validated methods (Palmeri et al., 2006). These simulations were performed under noise- and physiologic-motion free conditions in purely elastic media and were used to characterize the accuracy and precision of the proposed Lateral TTP calculation. The tracking beam configuration that was simulated is outlined in Table 1.

Experimental Methods A modified Siemens SONOLINE™ Antares scanner (Siemens Medical Solutions USA, Inc., Ultrasound Division, Issaquah, Wash., USA) was utilized for all experiments. Different transducers and system parameters were used for each experiment, depending upon the depth of the region of interest (ROI), and are specified in the experiment-specific sections that follow.

For all experiments, custom bean sequences were programmed into the scanner and either radio-frequency (RF) or the real and imaginary (IQ) components of the RF tracking data were stored for offline processing using custom written calculations (described below) on a Linux Beowulf cluster. IQ data were acquired using 4:1 parallel receive mode, where 4 receive beams are acquired for each tracking transmit beam (Dahl et al., 2007), while RF data was acquired in conventional receive mode (1:1) for the gelatin phantom study. Each interrogation consisted of a reference tracking pulse (conventional B-mode pulse) followed by high intensity pushing pulse and a series of tracking pulses to track the displacement and full recovery of the material after excitation. Further details of this procedure are covered by Dahl et al. (Dahl et al., 2007).

The size of the ROI for estimating shear wave speed is large relative to the ROE and cannot be adequately characterized with only 4 tracking beams after a single excitation. To fully characterize the shear wave propagating across the ROI, nine interrogations of the reference:push:tracking sequence were fired, where the excitation remained in the same location (at a lateral position of 0 in all of the images herein), but the tracking beams were offset at greater lateral positions from the excitation with each repetition. Displacements were estimated using either Loupas' method on IQ data or normalized cross-correlation with a 1.5λ kernel with 99% overlap on the RF data, as detailed by Pinton et al. (Pinton et al., 2006).

Motion Filtering For all in vivo datasets, a linear motion filter with a temporal range that varied as a function of lateral offset from the ROE was applied to remove physiologic motion from the displacement data. The temporal range was chosen to coincide with when 14 a shear wave was expected to travel through a given lateral position ($x_{lat}$) in the ROI. For each $x_{lat}$, the earliest time for the first non-zero displacement due to the propagating shear wave ($t_{startMin}$) was computed as:

$$t_{startMin} = T_{exc} + x_{lat} c_{Tmax} - 3*BW\ c_{Tmax} \quad (4)$$

where $T_{exc}$ was the duration of the excitation, BW was −6 dB lateral beamwidth (z d) of the excitation beam in the DOF that approximates the spatial extent of the propagating shear wave, $c_{Tmax}$ was the maximum shear wave speed that is expected in the material being imaged, and $c_{Tmin}$ was the minimum expected shear wave speed. Three times the −6 dB lateral beamwidth of the excitation beam was empirically chosen as a conservative estimate to estimate >95% of the shear wave's spatial extent. The latest time that a shear wave was expected to pass through a given lateral position ($t_{stopMax}$) was computed as:

$$t_{stopMax} = T_{swMax} + t_{startMax}, \quad (5)$$

where $T_{swMax}$ was the maximum expected shear wave period, and tstartMax was the latest time when a shear wave would have started passing through $x_{lat}$ The residual displacement was measured at $t_{stopMax}$, when the tissue should have fully recovered from the excitation. This residual displacement at $t_{stopMax}$ was used to subtract a linear displacement artifact through time based on the displacement at $t_{startMin}$, before which no displacement due to the propagating shear wave is expected. This filter removes transducer and physiologic motion, in addition to low frequency artifacts that can arise from transducer heating and power supply variations.

Phantom Studies Phantom measurements were performed using a gelatin-based tissue-mimicking phantom (Hall T. J. et al., 1997) using the VF10-5 array and a calibrated tissue mimicking phantom (Computerized Imaging Reference Systems, Inc., Norfolk, Va.) using the PH4-1 and VF10-5 array setups, using the parameters detailed in Table 2. These studies were used to characterize the precision of the calculation empirically and to demonstrate the calculation's independence on the array/focal configuration used to generate and track the shear waves.

TABLE 2

|  | VF10-5 (Phantom) | PH4-1 (Phantom & Human) |
| --- | --- | --- |
| Excitation Frequency (MHz) | 6.7 | 2.2 |
| Excitation Duration (µs) | 45 | 180 |
| Excitation F/# | 2.5 | 2.0 |
| Excitation Focal Depth (mm) | 20 | 37.5 |
| Lateral Beam Spacing (mm) | 0.30 | 0.13 |
| Tracking Frequency (MHz) | 6.7 | 2.2 |
| Tracking Transmit F/# | 2.0 | 2.0 |
| Tracking Receive F/# | 0.5 | 0.5 |
| Elevation Focus (mm) | ~20 | ~70 |
| PRF of Track Lines (kHz) | 12.5 | 5.6 |
| Duration of Tracking (ms) | 8 | 14 |

Human Studies The feasibility of reconstructing hepatic shear moduli with the Lateral TTP calculation was also demonstrated in human volunteers with written consent under approval from the Duke University Medical Center IRB (#9328-06-12). An intercostal imaging approach was used in all volunteers, with imaging performed between the ninth and tenth ribs, slightly anterior to the mid-axillary line. Six independent measurements were made during an imaging session, where a measurement consists of the transducer being placed in the intercostal space and the patient performing a full inspiration breath hold. Electrocardiogram (ECG) triggering was not utilized in this study, but could be added in future studies to potentially reduce cardiac motion artifacts. One of two individuals performed all of the volunteer scanning in these studies. Data were acquired using the procedure outlined above with the PH4-1 array with the Antares scanner, using the imaging parameters outlined in Table 2. Displacement tracking was performed using 4:1 parallel receive, where 4 receive beams were acquired for each tracking beam (Dahl et al., 2007). Displacements were estimated using the Loupas calculation on IQ data (Pinton et al., 2006) and motion filtering was performed as outlined in the earlier Motion Filtering section. The radiation force excitation power was chosen to achieve adequate displacement magnitudes (10-20 µm) within the ROE, while minimizing tissue heating. For these shear wave sequences (multiple excitations in a single location), validated FEM simulations indicate that the energy required to generate peak focal displacements of 20 µm per excitation in liver would result in a total cumulative temperature rise of less than 0.25° C. for less than 0.2 seconds of tissue insonification without taking into account perfusion effects that would lower heating estimates (Palmeri et al., 2004). The specifics of this thermal characterization are detailed in the Thermal Safety section. This heating is less than the 6° C. of heating that is accepted for diagnostic ultrasonic imaging per the US FDA (NCRP, 2002).

Thermal Safety Heating was empirically characterized using a thin-film thermocouple (TFT) embedded in tissue mimicking material (National Physical Laboratory, Teddington, UK) with an attenuation of 0.5 dB/cm/MHz, a specific heat of 3.9 MJ/K/m3, and a thermal conductivity of 0.52 W/m/K. Additional slabs of tissue mimicking material (TMM) were stacked on top of the embedded TFT until a height equal to the focal depth being evaluated was attained. Ultrasonic gel was used as coupling between these slabs, the transducer, and the TMM. The point of maximum temperature rise was detected by using LabView National Instruments, Austin, Tex.) and a stepping motor translation stage to move the transducer in 0.1 mm increments, transmit the ultrasonic pulse sequence of interest, and record the resulting temperature profile through time at each point. The temperature rise was calculated by applying a 0.02 s running average to the data and then subtracting the average ambient temperature recording over 3 s from the maximum temperature recorded.

Using this procedure, the maximum temperature for the PH4-1 configuration was measured to be 0.21±0.01° C. This heating was confirmed with matched simulations using the procedure outlined in Palmeri et al. (2004).

Simulations Simulation data were used to characterize the accuracy and precision of the Lateral TTP calculation for elastic materials with known shear moduli that were not corrupted by noise and/or motion artifacts. FIG. 8(a) shows the TTP displacement estimates as a function of lateral position extending away from the ROE at the excitation focal depth of 20 mm in elastic media with shear moduli of 1.33 and 2.83 kPa. The tracked simulation data were compiled over 20 independent speckle realizations. (The complete configurations of the simulated excitation and tracking beams are provided in Table 1.) FIG. 8(b) shows the reconstructed shear moduli at depths within the DOF of the excitation beam. As indicated on the FIGS. 8(a) and 8(b), both the non-tracked and tracked FEM data can be reconstructed within ±0.03 kPa of the 1.33 kPa material and ±0.08 kPa of the 2.83 kPa material for this demonstrative speckle realization.

Figure 9:
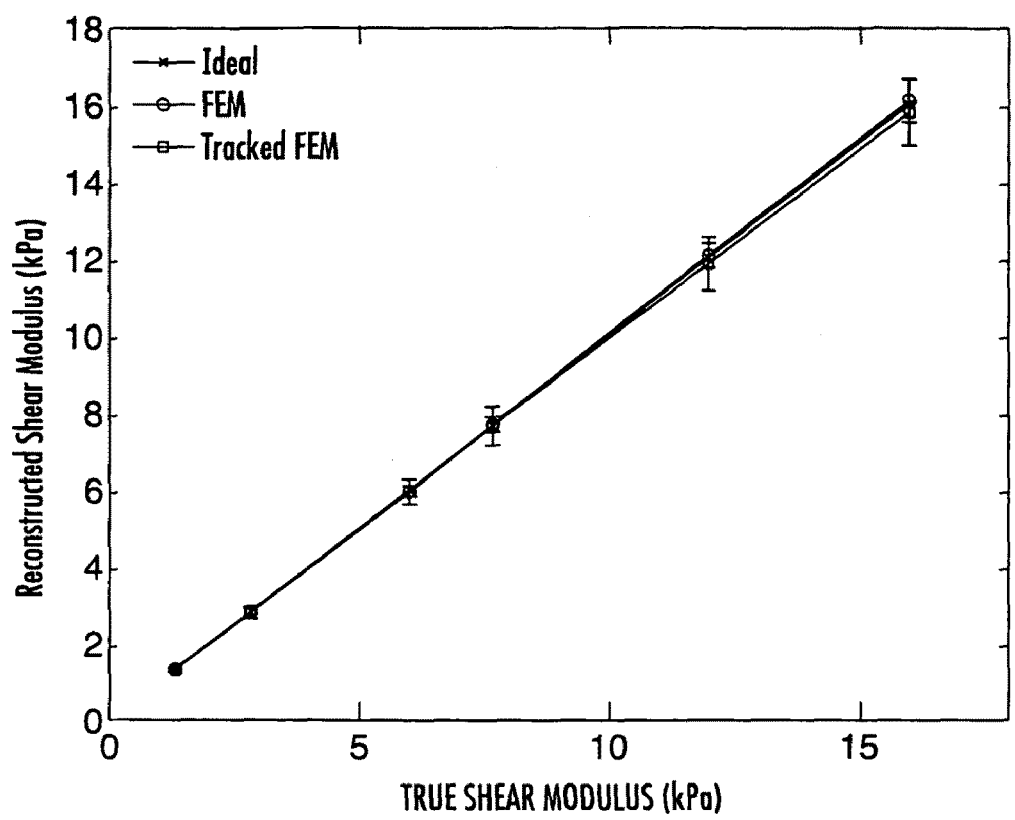
FIG. 9 is a graph of reconstructed shear moduli (kPa) as a function of true shear modulus (kPa) using the Lateral TTP calculation on ultrasonically-tracked and raw FEM displacement data for shear moduli ranging from 1.33-16 kPa. The error bars in the raw FEM data represent the variation in the reconstructed moduli over the DOF, while the error bars in the tracked FEM data represent the variation over 20 independent speckle realizations at the focal depth 20 mm.

The modulus reconstructions using the simulation data were then extended to a greater range of moduli that may be encountered when characterizing diseased (fibrotic) livers (Foucher et al., 2006; Sandrin et al., 2003). The shear modulus reconstructions for both raw FEM displacement data and ultrasonically-tracked FEM displacement data are shown in FIG. 9. The error bars associated with the nontracked FEM displacement data represent variations in the reconstructed moduli over the DOF, while the error bars associated with the tracked FEM data represent variations in the reconstructed moduli over 20 independent speckle realizations at the focal depth (20 mm).

Figure 10:
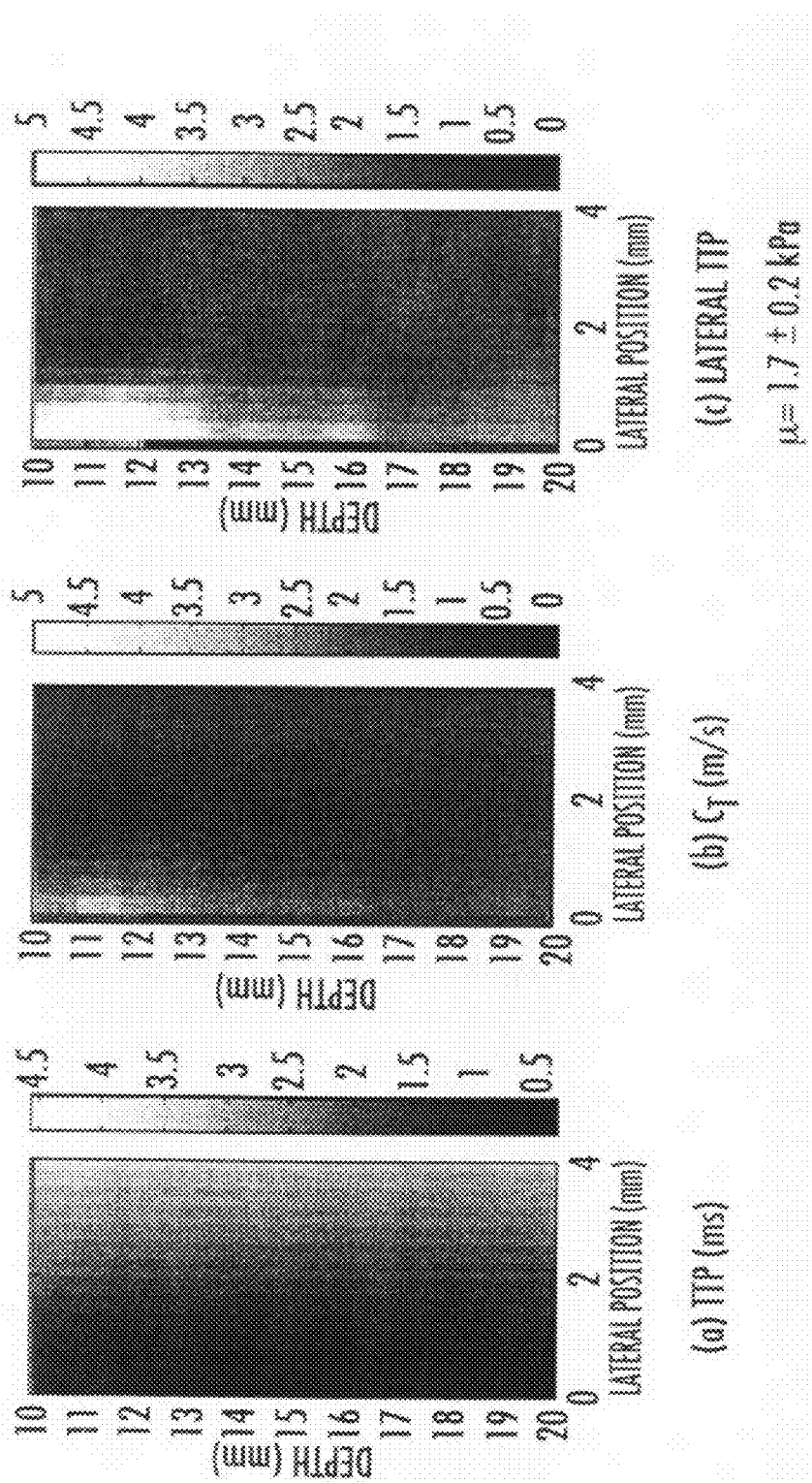
FIGS. 10($a$)-10($c$) are graphs of the sheer modulus reconstruction in an elastic gelatin phantom.

Phantoms The Lateral TTP calculation was applied to ARFI shear wave data obtained in a gelatin tissue-mimicking phantom (Hall T. J. et al., 1997; Palmeri et al., 2005). Two dimensional (2D) images of reconstructed shear moduli, as shown in FIGS. 10(a)-10(c), were made using the Lateral TTP calculation. The increased spatial resolution of the Lateral TTP calculation was achieved by reducing the lateral domain over which the linear regressions were performed on the TTP versus lateral position data. This implementation of the Lateral TTP calculation is similar to what would be achieved with differentiation of such data in Eikonal methods (McLaughlin and Renzi, 2006a,b), if the lateral extent of the linear regression was reduced to fewer points, approaching a local spatial derivative.

To demonstrate the independence of the Lateral TTP calculation on the excitation focal configuration and associated tracking configuration, a single location in a calibrated CIRS tissue-mimicking phantom was characterized 12 times using both the PH4-1 and the VF10-5 arrays. Both arrays were positioned so their lateral foci (F/2 focal configuration) occurred at the same phantom location, at a depth of 20 mm from the phantom surface. The VF10-5, which has an elevation focus near 19 mm, was operating at 5.7 MHz with a lateral focus at 20 mm. The PH4-1, which has an elevation focus near 70 mm, was operated at 2.2 MHz with a lateral focus at 37.5 mm (offset by a 17.5 mm water path standoff to image the same location as the more shallowly focused VF10-5 array). The PH4-1 characterization yielded a reconstructed shear modulus of 1.7±0.2 kPa, while the VF10-5 yielded a reconstructed shear modulus of 1.6±0.1 kPa.

In vivo Human Liver While the simulations and phantoms are good controls to test the accuracy and precision of the Lateral TTP calculation in reconstructing moduli, performing such reconstructions in vivo presents additional challenges, such as physiologic motion and the penetration of acoustic energy through skin and fat.

To demonstrate the feasibility of using the Lateral TTP calculation to longitudinally monitor liver stiffness in humans, two studies were conducted: (1) 20 human volunteers were imaged intercostally to reconstruct the shear moduli of their livers, and (2) two volunteers (7 and 8 from the 20 volunteer study) had their liver stiffness reconstructed 10 times over a 105 day period to evaluate the repeatability of such measurements. An intercostal imaging approach was chosen for these studies because it characterizes the same right posterior lobe of the liver that is typically biopsied by clinicians. Volunteers without known liver disease were chosen for these studies, but no definitive clinical studies (e.g., liver function tests or coagulation studies) were performed to confirm normal liver health. There were 10 male and 10 female volunteers with a mean age of 37 years (25-71 years old) and an average BMI of 23.5 (19.7-30.5).

FIGS. 11(a)-11(e) shows a demonstrative data set from Volunteer 16 (25 year old female, BMI 20). FIG. 11(a) shows the B-mode image with the ROI used for the shear wave speed characterization outlined by the yellow box. The motion-filtered displacement through time data at the focal depth are shown in FIG. 11(b); these data represent one of the depth increments processed over the entire DOF of the excitation beam. FIGS. 11(c) and 11(d) shows the times to peak displacement as a function of lateral position for all of the 0.5 mm increments over the DOF of the excitation beam before (FIG. 11(c)) and after (FIG. 11(d)) the goodness of fit metrics were applied to the data. FIG. 11(e) shows the reconstructed shear moduli over the 6 trials that were performed during the study, where each trial consisted of a new breath hold and repositioning of the transducer in the same intercostal space.

FIG. 12(a) shows the reconstructed shear moduli from all data that had regressions exceeding the goodness of fit metrics over the 6 trials (mean±one standard deviation) in the 20 human volunteers. (Note, there were not enough valid regressions for Volunteer 13 to provide a reliable shear modulus estimate.) FIG. 12(b) shows the repeated shear modulus reconstruction at 10 different time points over a 105 day period in two of the volunteers. As with the 20 volunteer study, each time point in the repeatability study consisted of 6 independent trials. (The absence of an estimate for Volunteer 7 on the first day was because the volunteer was not available for imaging that day, not because of an absence of valid shear modulus reconstructions.)

Figure 11:
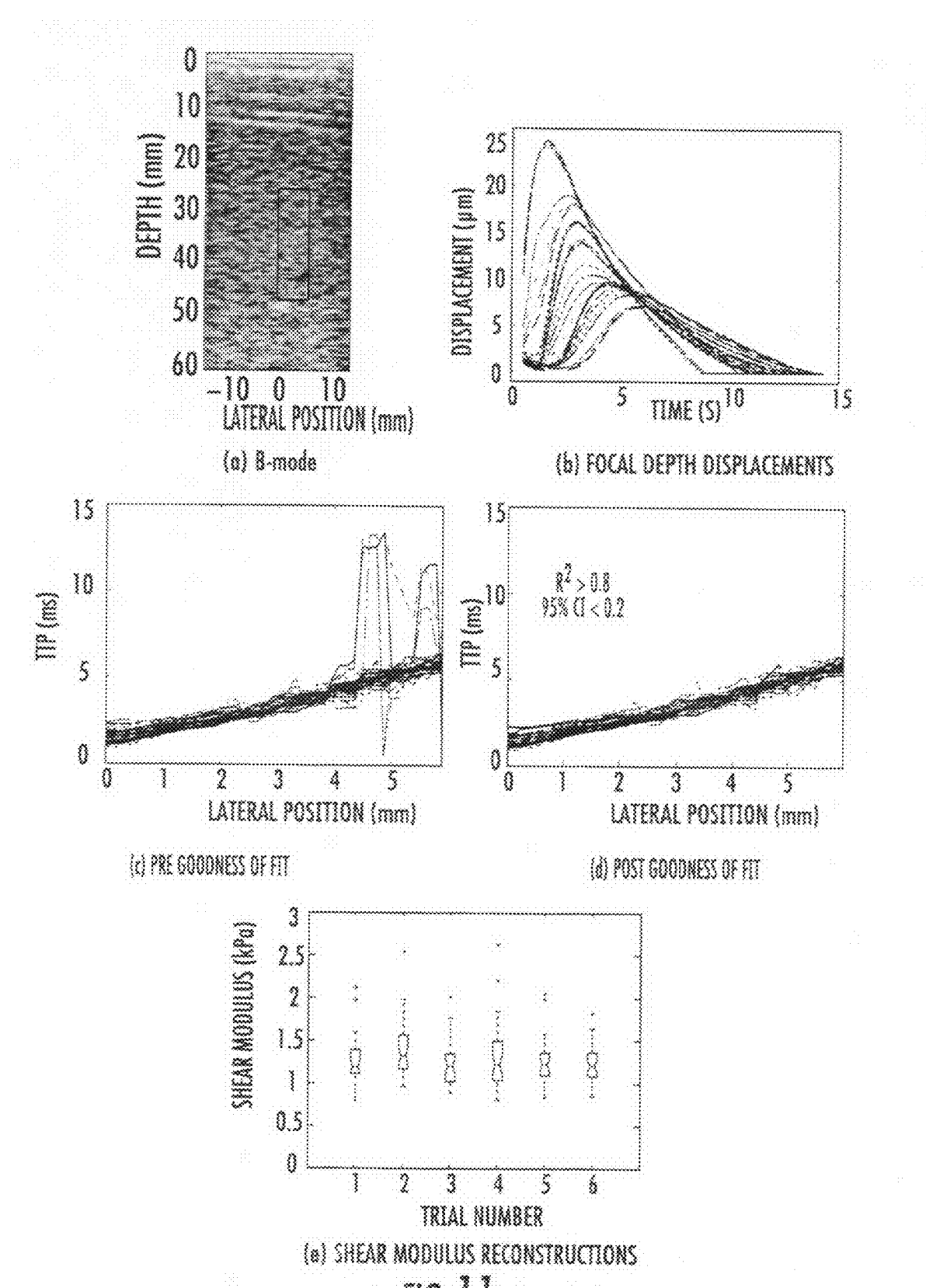
FIG. 11($a$) is a B-mode image from a human volunteer, with the ROI used for shear wave speed characterization by the Lateral TTP calculation outlined by the yellow box. The radiation force excitation was focused at 37.5 mm at a lateral position of zero.
Figure 12:
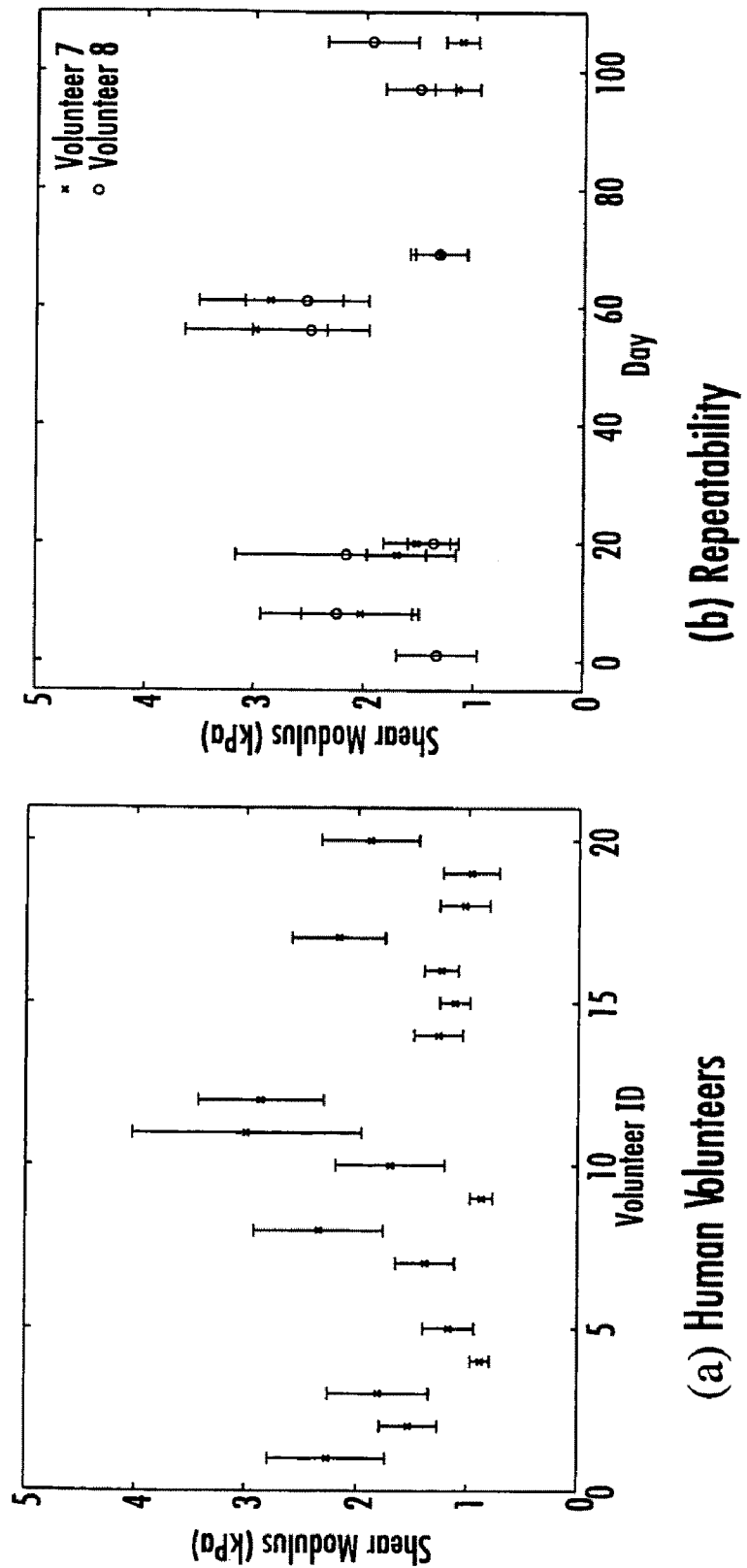
FIG. 12(a) is a graph of the in vivo liver shear moduli estimates in twenty human volunteers using an intercostals imaging approach between the ninth and tenth ribs.
FIG. 12(b) is a graph of a comparison of reconstructed in vivo liver shear moduli in two human volunteers over a four month period. Six measurements were performed intercostally on each day in each volunteer between the ninth and tenth ribs.
FIG. 12(c) is a graph of the mean reconstructed shear moduli in the 20 human volunteers as a function of their BMI. The left vertical dashed line represents the distinction between normal and overweight volunteers, and the right vertical dashed line represents the distinction between overweight and obsess volunteers.
Figure 12C:
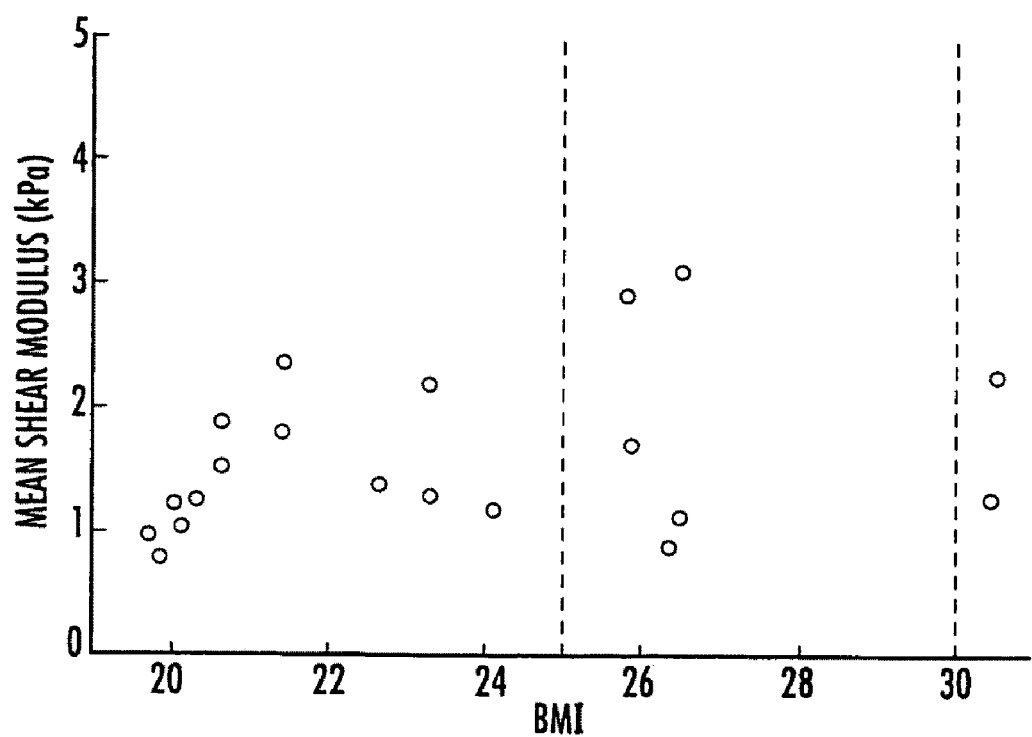

Discussion The data presented herein demonstrate the feasibility of using acoustic radiation force imaging methods to non-invasively quantify liver stiffness in vivo. The reconstructed shear moduli shown in FIGS. 11 and 12 are consistent with those reported for healthy human liver as determined by external excitation methods (e.g., the FibroScan® system (Sandrin et al., 2003; Foucher et al., 2006), assuming a relation of $\mu=\epsilon 3$). In a study by Rouviere et al. using MR elastography of the liver, the shear stiffness in healthy subjects was found to be 2.0±0.3 kPa (Roiviere et al., 2006), which agrees well with the data in the human volunteers (FIGS. 11 and 12). The error bars in these figures are greater than the standard deviations over the DOF associated with a single interrogation (FIG. 11(e)) because they include variability between 6 different interrogations, including variability in the region of liver that was interrogated. While it is assumed that the liver is homogeneous over the ROIs associated with a given interrogation, there may be heterogeneities between different interrogations depending on transducer location and depth of breath hold.

FIG. 12(b) shows that for the same two volunteers, reconstructed shear moduli varied between 1-3 kPa at 10 different time points over a 105 day period. There are several factors that may be affecting this variability, including when imaging is performed relative to eating, blood pressure, operator variability, and actual heterogeneity of stiffness within the liver. These factors are being investigated in greater detail in ongoing studies.

Figure 6:
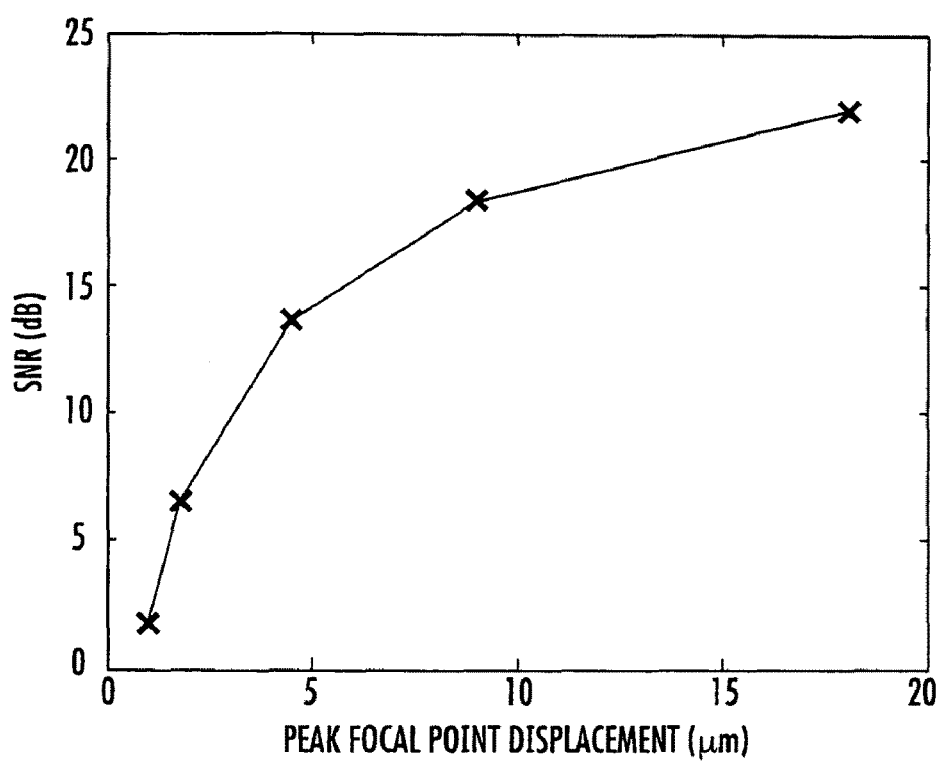
FIG. 6 is a graph if the peak displacement signal to noise ratio (SNR) over a 6 mm lateral range adjacent to the ROE as a function of peak focal point displacement ($\mu$m). The SNR was computed as the mean/standard deviation of peak displacement estimates over the 6 mm lateral range for 20 independent, simulated speckle realizations from FEM displacement data.

The SNR of the displacement estimates used to characterize shear wave propagation in vivo greatly impacts the success of the calculation (FIG. 6). Jitter in the displacement estimates increases with decreasing tracking beam frequency and is generally between 0.2-1 μm for the experimental setup presented herein (Walker and Traley, 1995). Clearly, the larger the signal (i.e., displacement due to radiation force excitation), the better the SNR (FIG. 6). In general, for all datasets, the number of good estimates (R2>0.8, 95% CI<0.2) increases with increasing displacement magnitude (SNR). It may be advantageous to generate peak focal displacements of at least 10 μm within the ROE and to restrict the lateral range over which linear regressions are performed to displacement magnitudes of at least 1 μm. It has also been observed that over repeated measurements at a given location, the peak focal displacement for a given transmit power can vary considerably, presumably due to differences in transducer coupling and differences in acoustic attenuation and aberration caused by tissue in the propagation path of the acoustic excitation.

Both the displacement magnitude and the thermal response of the tissue to acoustic excitation are linearly related to the in situ intensity of the acoustic pulse and the attenuation of the tissue (Equation 2), which are impacted by many factors, including: transmit beam parameters (frequency, F/#, and power), tissue absorption at the focus, and attenuation and aberration of the acoustic beam through intervening tissue. Limits on the maximum energy included in an interrogating beam arise from both the thermal response (for diagnostic ultrasonic imaging, total tissue temperature increase must be less than 6° C. (Herman and Harris, 2002)) and from system power output limitations. In the experimental implementation presented herein, the tissue is repeatedly excited in one spatial location in order to monitor shear wave propagation throughout a large lateral field of view (FOV). The use of 4:1 parallel receive tracking allows four lateral locations to be tracked for each excitation, reducing the total number of excitations by a factor of 4. This parallel receive implementation allows for either a reduction of the heat generated in the tissue or quadrupling the power in each excitation without any additional tissue heating. The tradeoff between lateral FOV size (the region over which shear wave propagation is monitored) and acoustic energy within each excitation (as determined both by tissue heating and system power output considerations) may also be considered.

A potential challenge for methods using acoustic radiation force to quantify elastic moduli in human liver in vivo are people who have "poor ultrasonic image quality". Acoustic waves pass through varying amounts of skin, connective tissue and fat before entering the liver, and such heterogeneous propagation paths can be associated with phase aberration, varying attenuation, and other effects that distort the distribution and decrease the magnitude of the acoustic energy within the focal region. For such cases, a potential solution would be to use lower frequency acoustic excitations, which are less susceptible to aberrations and near field energy loss.

The simulation and phantom experiment data (FIGS. 9 and 10) demonstrate the ability for the Lateral TTP calculation to accurately reconstruct the shear modulus of a material when the assumptions of material homogeneity and negligible dispersion are satisfied. These datasets are free of noise and physiologic motion, and they allow the theoretical performance of the calculation to be evaluated over the range of shear moduli that are expected in healthy and diseased livers. While the agreement between the reconstructed and actual moduli is good, the variance increases with stiffness. This effect is due to the fixed tracking beam pulse repetition frequency (PRF) that dictates the temporal sampling of the shear wave. As demonstrated in FIG. 7, the more compliant medium ($\mu=1.33$ kPa) has a slower shear wave speed and greater sampling per shear wavelength than the stiffer medium ($\mu=8$ kPa). This results in increased variance in the determination of the time of peak displacement in the stiffer medium. Clearly, increasing the PRF of the tracking beams would benefit estimates in stiffer media; however, as with conventional B-mode imaging, the maximum PRF is dictated by the focal depth and the propagation speed of the imaging pulse.

One of the benefits of the Helmholtz calculation is that a priori knowledge of the shear wave's propagation direction is not necessary. The Lateral TTP calculation, as implemented in this manuscript, has assumed that shear waves are propagating parallel to the lateral dimension (perpendicular to the central axis of the excitation), thus limiting the axial extent of its application to the DOF of the excitation beam, as demonstrated in FIG. 5. Incorporation of geometric compensations for shear wave propagation direction in the near field are under investigation, but decreased displacement magnitudes away from the focal zone will make reconstructions at these depths challenging. As demonstrated by the comparison of the VF10-5 and PH4-1 arrays in the phantom experiments, the configuration of the array used to generate the acoustic radiation force and track the resulting displacements should not impact the Lateral TTP calculation, as long as analysis is confined to the DOF.

In the current study, highly focused excitation beams (F/1.5 and F/2) were used to generate larger displacements because of the greater number of transmit elements. The depths over which this lateral propagation assumption is valid could be expanded by using larger F/# excitations to extend the DOF at the expense of using fewer excitation elements and generating less displacement. Another approach would be to implement sequences that interrogate multiple axial locations, either sequentially or in a rapid fire mode, as is performed in supersonic imaging, to simulate a 'line source' of shear waves, although the latter approach can be limited by system power constraints (Bercoff et al., 2004).

In addition to assuming that the direction of shear wave propagation is known, the Lateral TTP calculation also assumes that significant shear wave dispersion does not occur over the ROI that would cause distortion of the shear wave's shape and would reduce the correlation between the TTP displacement and the mean energy of the shear wave. Such dispersion would cause the TTP displacements to trend nonlinearly with respect to lateral position, making the linear regression assumptions invalid. Nonlinear TTP displacement relationships do not appear to pose a significant challenge in liver modulus quantification, but if present, this challenge could be reduced by restricting the regression domains, as was done in FIGS. 10(a)-10(c), or using a nonlinear fit to quantify the dispersion. Such trends would appear in the current implementation of the calculation as linear fits with poor goodness of fit metrics.

As demonstrated in FIG. 11(c-d), the goodness of fit metrics allow for TTP data that are corrupted by jitter, noise, and/or physiologic motion to be removed from the analysis without any user intervention. These goodness of fit metrics are responsible for the absence of a reconstructed shear modulus for volunteer 13 in FIG. 12(a).

The use of the linear motion filter applied over a dynamic temporal range that varies for each lateral position allows the underlying linear motion assumption to be restricted to a subdomain of the total temporal data acquired, making the assumption more valid. The use of higher-order filters (quadratic) has not yielded different results in liver data to date.

Overall, the human data presented herein demonstrate the feasibility of using acoustic radiation force methods to quantify liver moduli clinically, using an intercostal imaging approach that coincides with the location that liver biopsies are currently performed. While these results are promising, larger studies are necessary to optimize the imaging parameters and to confirm the clinical utility of these methods for diagnosing liver pathology.

Conclusions

Measurement of times to peak displacements at laterally offset positions within the depth of field of an acoustic radiation force excitation allows for accurate estimation of shear wave speeds and reconstruction of shear moduli in homogeneous elastic media. This approach, referred to herein as the Lateral TTP calculation, has been successfully validated in simulation and phantoms, and has been demonstrated in vivo in 20 human livers. The Lateral TTP calculation does not require second-order temporal and spatial differentiation of displacement data, as is done in Helmholtz reconstructions, but does rely on a presumed direction of shear wave propagation and minimal shear wave dispersion over the region of interest. Simulation studies indicate that shear moduli of healthy livers ($\mu$=0.8-3.0 kPa) can be reconstructed with a precision of 0.3 kPa, while more fibrotic tissues ($\mu$=10-15 kPa) can be reconstructed with a precision of 1.0 kPa. Liver modulus reconstructions have been successfully performed in vivo in human volunteers, with shear moduli (0.8-3.0 kPa) consistent with those reported in the literature. The ability to generate at least 10 µm displacements in the liver leads to increased valid shear wave reconstructions in vivo, and the application of linear regression goodness of fit metrics allows for data corrupted by noise and/or physiologic motion to be excluded from the analysis. These results demonstrate the feasibility of using radiation force methods to non-invasively quantify liver stiffness, which may be used clinically to correlate with liver fibrosis and to longitudinally monitor disease progression and aid in treatment decisions.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims.

REFERENCES

Bedossa P, Dargere D, Paradis V. Sampling variability of liver fibrosis in chronic hepatitis c. Hepatology 2003, 38(1): 1449-1457.

Bercoff J, Tanter M, Fink M. Supersonic shear imaging: A new technique for soft tissue elasticity mapping. IEEE Trans. Ultrason., Ferroelec., Freq. Contr. 2004, 51(4):396-409.

Christensen D. Ultrasonic Bioinstrumentation. New York: John Wiley & Sons, 1988.

Dahl J, Palmeri M, Agrawal V, Nightingale K, Trahey G. A parallel tracking method for acoustic radiation force impulse imaging. IEEE Trans. Ultrason., Ferroelec., Freq. Contr. 2007, 54(2):301-312.

Foucher J, Chanteloup E, Vergniol J, Castera L, LeBail B, Adhoute X, Bertet J,

Couzigou P, deLedinghen V. Diagnosis of cirrhosis by transient elastography (fibroscan): a prospective study. Gut 2006, 55(1):403-408. Foundation A. L. 2006. http://www.liverfoundation.org.

Greenleaf J, Fatemi M, Insana M. Selected methods for imaging elastic propoerties of biological tissues. Annu. Rev. Biomed. Eng. 2003, 5(1):57-78.

Hall T, Zhu Y, Spalding C. In vivo real-time freehand palpation imaging. Ultrasound Med. Biol. 2003, 29(3):427-435.

Hall T. J., Bilgen M., Insana M. F., Krouskop T. A. Phantom materials for elastography. IEEE Trans. Ultrason., Ferroelec., Freq. Contr. 1997, 44(6):1355-65.

Herman B, Harris G. Models and regulatory considerations for the transient temperature rise during diagnostic ultrasound pulses. Ultrasound in Medicine and Biology 2002, 28(9):1217-1224.

McLaughlin J, Renzi D. Shear wave speed recovery in transient elastography and supersonic imaging using propagating fronts. Inverse Problems 2006a, 22:681-706.

McLaughlin J, Renzi D. Using level set based inversion of arrival times to recover shear wave speed in transient elastography and supersonic imaging. Inverse Problems 2006b, 22:707-725.

NCRP. Report No. 140. Exposure Criteria for Medical Diagnostic Ultrasound: II. Criteria Based on All Known Mechanisms. NCRP Publications, Bethesda, Md. 20814: National Council on Radiation Protection and Measurements, 2002.

Nightingale K, McAleavey S, Trahey G. Shear wave generation using acoustic radiation force: in vivo and ex vivo results. Ultrasound Med. Biol. 2003, 29(12):1715-1723.

Nightingale K, Palmeri M, Trahey G. Analysis of contrast in images generated with transient acoustic radiation force. Ultrasound Med. Biol. 2006, 32(1):61-72.

Nyborg W. Acoustic streaming. In: Mason W, ed., Physical Acoustics, New York: Academic Press Inc, vol. IIB, chap. 11, 265-331. 1965.

Oliphant T, Manduca A, Elman R, Greenleaf J. Complex-valued stiffness reconstruction for magnetic resonance elastography by algebraic inversion of the differential equation. Magnetic Resonance in Medicine 2001, 45:299-310.

Ophir J, Cespedes I, Ponnekanti H, Yazdi Y, Li X. Elastography: A quantitative method for imaging the elasticity of biological tissues. Ultrasonic Imaging 1991, 13:111-134.

Palmeri M, Frinkley K, Nightingale K. Experimental studies of the thermal effects associated with radiation force imaging of soft tissue. Ultrasonic Imaging 2004, 26:100-114.

Palmeri M, McAleavey S, Trahey G, Nightingale K. Ultrasonic tracking of acoustic radiation force-induced displacements in homogeneous media. IEEE Trans. Ultrason., Ferroelec., Freq. Contr. 2006, 53(7)1300-1313.

Palmeri M, Sharma A, Bouchard R, Nightingale R, Nightingale K. A finite-element method model of soft tissue response to impulsive acoustic radiation force. IEEE Trans. Ultrason., Ferroelec., Freq. Contr. 2005, 52(10): 1699-1712.

Parker K. Ultrasonic attenuation and absorption in liver tissue. Ultrasound Med. Biol. 1983, 9(4):363-369.

Pinton G, Dahl J, Trahey G. Rapid tracking of small displacements with ultrasound. IEEE Trans. Ultrason., Felroelec., Freq. Contr. 2006, 53(6):1103-1117. Pinton G, Trahey G. Continuous delay estimation with polynomial splines. IEEE Trans. Ultrason., Ferroelec., Freq. Contr. 2006, 53(11):2026-2035.

Ratziu V, Charlotte F, Heurtier A, Gombert S, Giral P, Bruckert E, Grimaldi A, Carpon F, Poynard T. Sampling variability of liver biopsy in nonalcoholic fatty liver disease. Gastroenterology 2005, 128(1):1898-1906.

Regev A, Berho M, Jeffers L, Milikowski C, Molina E, Pyrsopoulos N, Feng Z, Reddy K, Schiff E. Sampling error and intrasobserver variation in liver biopsy in patients with chronic hcv infection. J. Gastroenterol. 2002, 97(1):2614-2618.

Roiviere O, Yin M, Dresner M, Rossman P, Burgart L, Fidler J, Ehman R. Mr elastography of the liver: Preliminary results. Radiology 2006, 240(2):440-448.

Sandrin L, Fourquet B, Hasquenoph J, Yon S, Fournier C, Mal F, Christidis C, Ziol M, Poulet B, Kazemi F, Beaugrand M, Palau R. Transient elastography: a new noninvasive method for assessment of hepatic fibrosis. Ultrasound Med. Biol. 2003, 29(12):1705-1713.

Sandrin L, Tanter M, Catheline S, Fink M. Shear modulus imaging with 2-D transient elastography. IEEE Trans. Ultrason., Ferroelec., Freq. Contr. 2002, 49(4):426-435.

Sarvazyan A, Rudenko O, Swanson S, Fowlkes J, Emelianov S. Shear wave elasticity imaging: A new ultrasonic technology of medical diagnostics. Ultrasound Med. Biol. 1998, 24(9):1419-1435.

Torr G. The acoustic radiation force. Am. J. Phys. 1984, 52:402-408. Walker W, Trahey G. A fundamental limit on delay estimation using partially correlated speckle signals. IEEE Trans. Ultrason., Ferroelec., Freq. Contr. 1995, 42(2):301-308.

That which is claimed is:

1. A method for determining a mechanical parameter of a sample, the method comprising:
   detecting shear waves that have been generated in the sample by an applied shear wave source along an axis of excitation;
   determining a time of peak displacement of the shear waves for a plurality of sample positions that are spatially offset from the axis of excitation; and
   determining at least one mechanical parameter of the sample based on the time of peak displacement for the plurality of sample positions that are spatially offset from the axis of excitation.

2. The method of claim 1, wherein the at least one mechanical parameter includes at least one of shear elasticity modulus, Young's modulus, dynamic shear viscosity, shear wave velocity and mechanical impedance of the sample.

3. The method of claim 1, wherein determining at least one mechanical parameter includes determining a slope of a plurality of times to peak displacement as a function of distance from an origin of the shear wave.

4. The method of claim 1, wherein the plurality of sample positions includes a plurality of lateral positions at a plurality of distances laterally displaced from an origin of the shear wave.

5. The method of claim 4, wherein the plurality of lateral positions includes a plurality of datasets, each dataset being obtained at a distance displaced from the origin of the shear wave at a predetermined transverse direction.

6. The method of claim 3, further comprising applying a regression coefficient threshold to the plurality of times to peak displacement.

7. The method of claim 3, wherein determining a slope includes determining a plurality of localized slopes of the times to peak displacements as a function of distance from the origin of the shear wave.

8. The method of claim 7, further comprising generating an image based on the plurality of localized slopes, wherein the localized slopes represent a spatial change in the mechanical property in the sample.

9. The method of claim 1, wherein the sample is an in vivo human tissue sample.

10. The method of claim 9, wherein the sample is a liver tissue sample.

11. The method of claim 1, wherein the shear waves are detected with an internally inserted ultrasound probe array.

12. The method of claim 1, wherein the shear waves are detected with an externally applied ultrasound array.

13. The method of claim 1, wherein the applied shear wave source is an ultrasound transducer.

14. The method of claim 13, wherein the shear waves are detected by the ultrasound transducer.

15. The method of claim 1, further comprising generating the shear waves by transmitting ultrasound energy into the sample in a first direction to provide a shear wave source that generates an extended shear wave that propagates in a second direction substantially orthogonal to the first direction to cause movement in the first direction of tissue that is offset from the shear wave source in the second direction.

16. The method of claim 9, further comprising correlating the at least one mechanical parameter of the sample to a measurement of a healthy/diseased tissue state.

17. The method of claim 9, further comprising:
   monitoring the at least one mechanical parameter of the sample as a function of time; and
   assessing a healthy/diseased tissue state based on a change in the at least one mechanical parameter of the sample as a function of time.

18. The method of claim 1, wherein the plurality of sample positions is along the axis of excitation of the applied shear wave source.

19. The method of claim 1, wherein determining the at least one mechanical parameter of the sample is based on a reference database of experimentally determined and/or simulated times of peak displacement and associated mechanical properties.

20. A system for determining a mechanical parameter of a sample, the system comprising:
   means for detecting shear waves that have been generated in the sample by an applied shear wave source along an axis of excitation;
   means for determining a time of peak displacement of the shear waves for a plurality of sample positions that are spatially offset from the axis of excitation; and
   means for determining at least one mechanical parameter of the sample based on the time of peak displacement for the plurality of sample positions that are spatially offset from the axis of excitation.

21. A system for determining a mechanical parameter of a sample, the system comprising:
a shear wave peak displacement module configured to detect shear waves that have been generated in a sample by an applied shear wave source along an axis of excitation, to determine a time of peak displacement of the shear waves for a plurality of sample positions that are spatially offset from the axis of excitation, and to determine at least one mechanical parameter of the sample based on the time of peak displacement for the plurality of sample positions that are spatially offset from the axis of excitation.

22. A computer program product for determining a mechanical parameter of a sample, the computer program product comprising non-transient computer readable storage medium having computer readable program code embodied therein, the computer readable program code comprising:
computer readable program code for detecting shear waves that have been generated in the sample by an applied shear wave source along an axis of excitation;
computer readable program code for determining a time of peak displacement of the shear waves for a plurality of sample positions that are spatially offset from the axis of excitation; and
computer readable program code for determining at least one mechanical parameter of the sample based on the time of peak displacement for the plurality of sample positions that are spatially offset from the axis of excitation.

* * * * *

UNITED STATES PATENT AND TRADEMARK OFFICE
CERTIFICATE OF CORRECTION

PATENT NO.        : 8,118,744 B2                              Page 1 of 1
APPLICATION NO.   : 12/028203
DATED             : February 21, 2012
INVENTOR(S)       : Palmeri et al.

It is certified that error appears in the above-identified patent and that said Letters Patent is hereby corrected as shown below:

In the Patent:

Column 20, Line 58: Please correct "of $\mu = \in 3$)." to read -- of $\mu = E3$). --

Signed and Sealed this
First Day of January, 2013

David J. Kappos
*Director of the United States Patent and Trademark Office*

UNITED STATES PATENT AND TRADEMARK OFFICE
CERTIFICATE OF CORRECTION

Page 1 of 1

PATENT NO. : 8,118,744 B2
APPLICATION NO. : 12/028203
DATED : February 21, 2012
INVENTOR(S) : Palmeri et al.

It is certified that error appears in the above-identified patent and that said Letters Patent is hereby corrected as shown below:

In the Specification:
Column 1, Lines 14-18, STATEMENT OF GOVERNMENT SUPPORT: Please replace the paragraph in its entirety with the following:

This invention was made with Government support under grant numbers R01-CA114075 and R01-EB002132 awarded by the National Institute of Health and grant number 2003014921 awarded by National Science Foundation. The Government has certain rights to this invention.

Signed and Sealed this
Fifteenth Day of April, 2014

Michelle K. Lee
*Deputy Director of the United States Patent and Trademark Office*